US006936698B2

(12) United States Patent
Taylor

(10) Patent No.: US 6,936,698 B2
(45) Date of Patent: Aug. 30, 2005

(54) MONOCLONAL ANTIBODIES WITH REDUCED IMMUNOGENICITY

(75) Inventor: Alexander H. Taylor, Exton, PA (US)

(73) Assignee: SmithKline Beecham, Philadelphia, PA (US)

( * ) Notice: Subject to any disclaimer, the term of this patent is extended or adjusted under 35 U.S.C. 154(b) by 0 days.

(21) Appl. No.: 09/905,243

(22) Filed: Jul. 16, 2001

(65) Prior Publication Data

US 2002/0062009 A1 May 23, 2002

Related U.S. Application Data

(63) Continuation of application No. 09/300,970, filed on Apr. 28, 1999, now abandoned.
(60) Provisional application No. 60/083,367, filed on Apr. 28, 1998.

(51) Int. Cl.⁷ .............................................. C07K 16/00
(52) U.S. Cl. ................... 530/387.3; 424/133.1
(58) Field of Search .......................... 530/387.1, 387.3; 424/130.1, 133.1

(56) References Cited

U.S. PATENT DOCUMENTS

| | | | |
|---|---|---|---|
| 5,225,539 A | | 7/1993 | Winter |
| 5,558,864 A | | 9/1996 | Bendig et al. |
| 5,585,089 A | | 12/1996 | Queen et al. |
| 5,639,641 A | | 6/1997 | Pedersen et al. |
| 5,693,761 A | | 12/1997 | Queen et al. |
| 5,693,762 A | * | 12/1997 | Queen et al. |
| 5,756,096 A | * | 5/1998 | Newman et al. |
| 5,800,988 A | | 9/1998 | Casterman et al. |
| 5,856,135 A | | 1/1999 | Tsuchiya et al. |

FOREIGN PATENT DOCUMENTS

| | | | |
|---|---|---|---|
| WO | WO 91/09967 | * | 7/1991 |
| WO | WO 93/02108 | | 2/1993 |
| WO | WO 93/17105 | | 9/1993 |
| WO | WO 96/16990 | | 6/1996 |

OTHER PUBLICATIONS

Co et al (PNAS 88:2869–2873, 1991).*
Colnot et al (Cancer Immunol Immunother. 52:576–82, 2003 abstract.*
Cobleigh et al (J of Clinical Oncology 17:2639–2648, 1999.*
Panka et al., PNAS 85:3080–3084, 1988.*
Amit et al., Science 233:747, 1986.*
Rudikoff et al., PNAS 79:1979–1983, 1982.*
Vijh–Warrier et al., Molecular Immunology 32:1081–1092, 1995.*
Greenspan, NS, Bona, CA. *Idiotypes:structures and immunogenicity. FASEB J.* (1993) Mar.;7(5):436–44. Abstract.
Kuus–Reichel, et al. *Will Immunogenicity Limit the Use, Efficacy, and Future Development of Therapeutic Monoclonal Antibodies? Clinical and Diagnostic Laboratory Immunology.* Jul. 1994, 1(4):365–372.
S. Tonegawa, "Somatic Generation of Antibody Diversity", *Nature*, vol. 302, pp. 575–581 (1983).
Vigh–Warrier, et al. "Characterization of the Variable Regions of a Chimpanzee Monoclonal Antibody with Potent Neutralizing Activity Against HIV–1", *Molecular Immunology*, vol. 32, pp. 1081–1092 (1995).
Anderson et al. "A Primatized Mab to Human CD4 Causes Receptor Modulation, without Marked Reduction in CD4⁺T Cells in Chimpazees: In Vitro and in Vivo Characterization of a Mab (IDEC–CE9.1) to Human CD4", *Clinical Immunology and Immunopathology*, vol. 84, No. 1, pp. 73–84 (1997).
Kettleborough, et al., "Humanization of a Mouse Monoclonal Antibody by CDR–Grafting: the Importance of Framework Residues on Loop Conformation," *Protein Engineering*, 4(7):773–783 (1991).
Riechmann, et al., "Reshaping Human Antibodies for Therapy," *Nature*, 332(6162):323–327 (Mar. 24, 1998).
Queen, et al., "A Humanized Antibody that Bind to the Interleukin 2 Receptor," *Proceedings of the National Academy of Sciences of USA*, 86(24):10029–10033 (Dec. 1, 1989).
Mary M. Bending, "Humanization of Rodent Monoclonal Antibodies by CDR Grafting," *Methods: A Companion to Methods in Enzymology*, 8:83–93 (1995).
Lewis, et al., "Cloning and Sequence Analysis of κ and γ Cynomolgus Monkey Immunoglobulin cDNA's," *Developmental and Comparative Immunology*, 17(6):549–560 (1993).

* cited by examiner

*Primary Examiner*—Larry R. Helms
(74) *Attorney, Agent, or Firm*—Andrea V. Lockenour; Elizabeth J. Hecht; Edward R. Gimmi

(57) ABSTRACT

Antibodies having reduced immunogenicity and methods for making them are disclosed.

14 Claims, 6 Drawing Sheets

Figure 1

```
       ****
4A6    DTVLTQSPA   LAVPPGERVT  VSCRASESVS  TFLHWYQQKP  GHQP
C108G  AVHMTQSPSS  LSASVGDSVT  ITCRASQTIN  IYLNWYQQKP  GKAP
           *           *

4A6    KLLIYLASKL  ESGVPARFSG  GGSGTDFTLT  IDPVEADDTA  TYYCQQTWND
C108G  KLLIFDASIL  QSGVPSRFSG  SGSGTDFSLT  IRSLQPEDFA  TYYCQCGWGTH

4A6    PRTFGGGT  KLELKR
C108G  PYNFGQGT  KLEIKR
```

Figure 2

```
              *    *               *
4A6   EVQLQQSGPE VGRPGSSVKI SCKASGYTFT DYVLNWVK QSPGQGLEWI
C108G EVQLVESGGG VVQPGGSLRL SCAASGFTFD DFAMHWVR QAPGKGLEWI

*                    ** * *      *
4A6   GWIDPDYG  TTDYAEKFKK KATLTADTSS STAYIQLSSL TSEDTATYFC
C108G SLVSWDSY  NIYHADSVKG RFTISRDNSR NSLYLQMNDL RPEDTAIYFC

*
4A6   ARSRNYGG.. ........YI NYWGQGVMVTVS
C108G AKADTGGDFD YVSDSWRCAL DYWGQGTLVTVS
```

Figure 3

```
          1                                   CDR1
VLB9      DIQMTQTTSS LSASLGDRVT ITCRSSQ.......DISNFLN WYQQKPDGTV
Cmp46-3   DIQMTQSPSS LSASVGDRVT ITCRASQ.......GISNYLA WYQQKPGKAP

45   CDR2                                       CDR3  94
VLB9      KLLIYYTSTL HSGVPSRFSG SGSGTDYSLT ISNLEQEDIA TYFCQQGNTL
Cmp46-3   KLLIYYASRL ESGVPSRFSG SGSGTDYTLT ISSLQPEDFA TYYCQQYNSN

95
VLB9      P..WTFGGGT NLEIKR
cmp46-1        FGGGT KVEIKR
```

Figure 4

```
              1          11         21                CDR1       39         48
                                            *   *                *          *
VHB9        QVQLQQSGAE LMKPGASVKI SCKATGYTFS SYWIE..WVK QRPGHGLEWI
AMP41CL18   QVQLVQSGAE VKKPGSSVKV SCKVSGGTFS TYGFS..WVR QAPGQGLEWM

49         CDR2       66         76         83         92
                                  ** *
VHB9        GEILP..RSG NTNYNEKFKG KATFTAETSS NTAYMQLSSL TPEDSAVYYC
AMP41CL18   GMIIP..IVG TVKYAQRFQG RVSINADTST NIAYMELTSL RSEDTAVYYC

93    CDR3             104
                 **
VHB9        SSRGVRGSM.........DYW GQGTSVTVSS
AMP41CL18   ATDLTVTTNDAF......DI
AMP41CL10                       W GQGTLVTVSS
```

Figure 5

```
            1                                       CDR1
            *
VL3G9       DIVMTQSQKF MSTSVGDRVS VTCKASQ.......NVGTNVA WYQQKPGQSP
VK46-14     DIQMTQSPSS LSASVGDRVT ITCRASQ.......SISNYLS WYQQKPGKAP

45    CDR2                                      CDR3  94
            *              *
VL3G9       KALIYSASYR YSGVPDRFTG SGSGTDFTLT ISNVQSEDLA EYFCQQYNSY
VK46-14     KLLIYYASTL QSGVPSRFSG SGSGTDFTLT ISSLQPEDFA TYYCQHGYGT

95
VL3G9       P..LTFGAGT KLELK
VK46-14     H..PTFGGGT KVEIK
```

Figure 6

```
               1          11         21              CDR1    39          48
                                        *  *  *              *            *
VH3G9      QVQLQQPGAE LVKSGASVKL SCKASGSTFT SYWMH..WVK QRPGRGLEWI
Chimp41-18 QVQLVQSGAE VKKPGSSVKV SCKVSGGTFS TYGFS..WVR QAPGQGLEWM 49         CDR2       66         76         83          92
                           ****  *  *
VH3G9       GRIDP..NSG GTKDNEKFKS KATLTVDKPS STAYMQLSSL TSEDSAVYYC
Chimp41-18  GMIIP..IVG TVKYAQRFQG RVSINADTST NIAYMELTSL RSEDTAVYYC 93   CDR3           104
                 *
VH3G9       ARETYYDSS.......FAYW GQGTLVTVS
Chimp41-18  ATDLTVTTN......DAFDIW GQGTMVTVS
```

SEQUENCE LISTING

<160> NUMBER OF SEQ ID NOS: 97

<210> SEQ ID NO 1
<211> LENGTH: 429
<212> TYPE: DNA
<213> ORGANISM: Pan troglodytes
<220> FEATURE:
<221> NAME/KEY: CDS
<222> LOCATION: (1)...(429)

<400> SEQUENCE: 1

| atg | aaa | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |

| gtc | ctg | tcc | cag | gtg | cag | ttg | cag | gag | tcg | ggc | cca | gga | ctg | gtg | aag | 96 |
| Val | Leu | Ser | Gln | Val | Gln | Leu | Gln | Glu | Ser | Gly | Pro | Gly | Leu | Val | Lys | |
| | | | 20 | | | | | 25 | | | | | 30 | | | |

| cct | tca | cag | acc | ttg | tcc | ctg | acc | tgc | gct | gtg | tct | ggt | ggc | tcc | atc | 144 |
| Pro | Ser | Gln | Thr | Leu | Ser | Leu | Thr | Cys | Ala | Val | Ser | Gly | Gly | Ser | Ile | |
| | | | 35 | | | | | 40 | | | | | 45 | | | |

| act | agt | gct | tac | tac | tat | tgg | agc | tgg | atc | cgc | cag | tca | cca | ggg | aag | 192 |
| Thr | Ser | Ala | Tyr | Tyr | Tyr | Trp | Ser | Trp | Ile | Arg | Gln | Ser | Pro | Gly | Lys | |
| 50 | | | | | 55 | | | | | 60 | | | | | | |

| gga | ctg | gag | tgg | att | ggg | agt | atc | tat | tat | agt | ggg | acc | att | ttc | tcc | 240 |
| Gly | Leu | Glu | Trp | Ile | Gly | Ser | Ile | Tyr | Tyr | Ser | Gly | Thr | Ile | Phe | Ser | |
| 65 | | | | | 70 | | | | | 75 | | | | | 80 | |

| aac | cca | tcc | ctc | aag | agt | cga | gtc | gcc | atg | tca | gta | ggc | acg | tcc | aag | 288 |
| Asn | Pro | Ser | Leu | Lys | Ser | Arg | Val | Ala | Met | Ser | Val | Gly | Thr | Ser | Lys | |
| | | | | 85 | | | | | 90 | | | | | 95 | | |

| acc | cag | ttc | tcc | ctg | agc | ttg | agt | tct | gtg | acc | gcc | gcg | gac | acg | gcc | 336 |
| Thr | Gln | Phe | Ser | Leu | Ser | Leu | Ser | Ser | Val | Thr | Ala | Ala | Asp | Thr | Ala | |
| | | | | 100 | | | | | 105 | | | | | 110 | | |

| gtg | tac | tac | tgt | gcg | aga | ggt | ctg | ctc | ctc | acc | att | gga | ctg | acc | aac | 384 |
| Val | Tyr | Tyr | Cys | Ala | Arg | Gly | Leu | Leu | Leu | Thr | Ile | Gly | Leu | Thr | Asn | |
| | | 115 | | | | | 120 | | | | | 125 | | | | |

| tac | tac | ttt | gac | tac | tgg | ggc | ccg | gga | acc | ctg | gtc | acc | gtc | ttc | | 429 |
| Tyr | Tyr | Phe | Asp | Tyr | Trp | Gly | Pro | Gly | Thr | Leu | Val | Thr | Val | Phe | | |
| 130 | | | | | 135 | | | | | 140 | | | | | | |

<210> SEQ ID NO 2
<211> LENGTH: 414
<212> TYPE: DNA
<213> ORGANISM: Pan troglodytes
<220> FEATURE:
<221> NAME/KEY: CDS
<222> LOCATION: (1)...(414)

<400> SEQUENCE: 2

| atg | aaa | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |

| gtc | ctg | tcc | cag | gtg | cag | cta | cag | gag | tcg | ggc | cca | gga | cta | gtg | aag | 96 |
| Val | Leu | Ser | Gln | Val | Gln | Leu | Gln | Glu | Ser | Gly | Pro | Gly | Leu | Val | Lys | |
| | | | 20 | | | | | 25 | | | | | 30 | | | |

| ccg | tca | cag | acc | ctg | tcc | ctc | acc | tgc | ggt | gtc | tct | ggt | gcc | tcc | atc | 144 |
| Pro | Ser | Gln | Thr | Leu | Ser | Leu | Thr | Cys | Gly | Val | Ser | Gly | Ala | Ser | Ile | |
| | | | 35 | | | | | 40 | | | | | 45 | | | |

| aat | agt | ggt | gtt | cat | tac | tgg | gcc | tgg | ata | cgc | cag | cct | gca | gga | aag | 192 |
| Asn | Ser | Gly | Val | His | Tyr | Trp | Ala | Trp | Ile | Arg | Gln | Pro | Ala | Gly | Lys | |
| 50 | | | | | 55 | | | | | 60 | | | | | | |

| gga | ctg | gag | tgg | att | ggc | aat | atc | tat | cat | agt | ggg | agc | gcc | tac | tac | 240 |
| Gly | Leu | Glu | Trp | Ile | Gly | Asn | Ile | Tyr | His | Ser | Gly | Ser | Ala | Tyr | Tyr | |

```
                Gly Leu Glu Trp Ile Gly Asn Ile Tyr His Ser Gly Ser Ala Tyr Tyr
                 65                  70                  75                  80 act cca tcc ctc gag agt cga gtc tcc atg tca ata gag acg tcc aag              288
Thr Pro Ser Leu Glu Ser Arg Val Ser Met Ser Ile Glu Thr Ser Lys
                 85                  90                  95 agc cag ttc ttc cta aac tta aat tct ctg acc gcc gcg gac acg gct              336
Ser Gln Phe Phe Leu Asn Leu Asn Ser Leu Thr Ala Ala Asp Thr Ala
            100                 105                 110 atc tat tat tgt gcg aga cga cat act tcg tca gac tac ttt gac ttt              384
Ile Tyr Tyr Cys Ala Arg Arg His Thr Ser Ser Asp Tyr Phe Asp Phe
            115                 120                 125 tgg ggc cgc gga atc ctg gtc atc gtc tcc                                      414
Trp Gly Arg Gly Ile Leu Val Ile Val Ser
130                 135

<210> SEQ ID NO 3
<211> LENGTH: 427
<212> TYPE: DNA
<213> ORGANISM: Pan troglodytes
<220> FEATURE:
<221> NAME/KEY: CDS
<222> LOCATION: (1)...(427)

<400> SEQUENCE: 3 atg ggg tca acc gcc atc ctc gcc ctc ctc ctg gct gtt ctc gaa gga               48
Met Gly Ser Thr Ala Ile Leu Ala Leu Leu Leu Ala Val Leu Glu Gly
  1               5                  10                  15 gtc cgt gca gac gtg cag ctg gtg cag tcc gga gca gag gtg aaa aag               96
Val Arg Ala Asp Val Gln Leu Val Gln Ser Gly Ala Glu Val Lys Lys
             20                  25                  30 ccc ggg gag tct ctg aag atc tcc tgt aag gtc tct gga aat gaa ttt              144
Pro Gly Glu Ser Leu Lys Ile Ser Cys Lys Val Ser Gly Asn Glu Phe
         35                  40                  45 acc aac tac tgg atc gcc tgg gtg cgc cag atg tcc ggg aaa ggc ctg              192
Thr Asn Tyr Trp Ile Ala Trp Val Arg Gln Met Ser Gly Lys Gly Leu
     50                  55                  60 gag tgg atg ggg agc atc tat cct ggt gac tct gat acc aga tac aac              240
Glu Trp Met Gly Ser Ile Tyr Pro Gly Asp Ser Asp Thr Arg Tyr Asn
 65                  70                  75                  80 ccg tcc ttc caa ggc caa gtc acc ttt tca gcc gac aag tcc atc acc              288
Pro Ser Phe Gln Gly Gln Val Thr Phe Ser Ala Asp Lys Ser Ile Thr
             85                  90                  95 acc gcc tat ttg cag tgg agt agt ctg gag gcc tcg gac acc gcc atg              336
Thr Ala Tyr Leu Gln Trp Ser Ser Leu Glu Ala Ser Asp Thr Ala Met
        100                 105                 110 tac tac tgt gcg agc cga aat cac ttt gtt ttc ggg gaa gtt att act              384
Tyr Tyr Cys Ala Ser Arg Asn His Phe Val Phe Gly Glu Val Ile Thr
        115                 120                 125 act ttg acg gct ggg gcc agg gaa acc ctg ggt cac cgt ctc c                    427
Thr Leu Thr Ala Gly Ala Arg Glu Thr Leu Gly His Arg Leu
        130                 135                 140

<210> SEQ ID NO 4
<211> LENGTH: 402
<212> TYPE: DNA
<213> ORGANISM: Pan troglodytes
<220> FEATURE:
<221> NAME/KEY: CDS
<222> LOCATION: (1)...(402)

<400> SEQUENCE: 4 ttg ggg ctc cgc tgg gtt ttc ctt gtt gct ttt tta gaa ggt gtc cag               48
Leu Gly Leu Arg Trp Val Phe Leu Val Ala Phe Leu Glu Gly Val Gln
```

-continued

```
          1                   5                  10                  15
tgt gag gta cag ctg gtg gag tct ggg gga ggc ttg gta cag cct ggg      96
Cys Glu Val Gln Leu Val Glu Ser Gly Gly Gly Leu Val Gln Pro Gly
             20                  25                  30 ggg tcc ttg aca ctc tcc tgt gca gcc tct gga ttc acc ttc agt agg     144
Gly Ser Leu Thr Leu Ser Cys Ala Ala Ser Gly Phe Thr Phe Ser Arg
         35                  40                  45 agt ggc atg cac tgg gtc cgc cag gct cca ggg aag gga ctg ggg tgg     192
Ser Gly Met His Trp Val Arg Gln Ala Pro Gly Lys Gly Leu Gly Trp
     50                  55                  60 ctt gca tac att gat tat ggc agt att ttc ata tac tac tcg gac tca     240
Leu Ala Tyr Ile Asp Tyr Gly Ser Ile Phe Ile Tyr Tyr Ser Asp Ser
 65                  70                  75                  80 gtg aag ggc cgc ttc acc atc tcc aga gac aac gcc aag aat tca ctc     288
Val Lys Gly Arg Phe Thr Ile Ser Arg Asp Asn Ala Lys Asn Ser Leu
                 85                  90                  95 tat ctg caa atg aac agc ctg aga gcc gac gac acg gct ttt tat tac     336
Tyr Leu Gln Met Asn Ser Leu Arg Ala Asp Asp Thr Ala Phe Tyr Tyr
             100                 105                 110 tgt acg acc cat aat tgg ggg gag tta act gac tac tgg ggc cag gga     384
Cys Thr Thr His Asn Trp Gly Glu Leu Thr Asp Tyr Trp Gly Gln Gly
         115                 120                 125 acc ctg gtc acc gtc tcc                                             402
Thr Leu Val Thr Val Ser
             130

<210> SEQ ID NO 5
<211> LENGTH: 408
<212> TYPE: DNA
<213> ORGANISM: Pan troglodytes
<220> FEATURE:
<221> NAME/KEY: CDS
<222> LOCATION: (1)...(408)

<400> SEQUENCE: 5 atg gaa ttg ggg ctc cgc tgg gtt ttc ctt gtt gct ttt tta gaa ggt      48
Met Glu Leu Gly Leu Arg Trp Val Phe Leu Val Ala Phe Leu Glu Gly
  1               5                  10                  15 gtc cag tgt gag gta cag ctg gtg gag tct ggg gga ggc ttg gta cag      96
Val Gln Cys Glu Val Gln Leu Val Glu Ser Gly Gly Gly Leu Val Gln
                 20                  25                  30 cct ggg ggg tcc ttg aca ctc tcc tgt gca gcc tct gga ttc acc ttc     144
Pro Gly Gly Ser Leu Thr Leu Ser Cys Ala Ala Ser Gly Phe Thr Phe
             35                  40                  45 agt agg agt ggc atg cac tgg gtc cgc cag gct cca ggg aag gga ctg     192
Ser Arg Ser Gly Met His Trp Val Arg Gln Ala Pro Gly Lys Gly Leu
         50                  55                  60 gag tgg ctt gca tac att gat tat ggc agt att ttc ata tac tac tcg     240
Glu Trp Leu Ala Tyr Ile Asp Tyr Gly Ser Ile Phe Ile Tyr Tyr Ser
 65                  70                  75                  80 gac tca gtg aag ggc cgc ttc acc atc tcc aga gac aac gcc aag aat     288
Asp Ser Val Lys Gly Arg Phe Thr Ile Ser Arg Asp Asn Ala Lys Asn
                 85                  90                  95 tca ctc tat ctg caa atg aac agc ctg aga gcc gac gac acg gct ttt     336
Ser Leu Tyr Leu Gln Met Asn Ser Leu Arg Ala Asp Asp Thr Ala Phe
             100                 105                 110 tat tac tgt acg acc cat aat tgg ggg gag tta act gac tac tgg ggc     384
Tyr Tyr Cys Thr Thr His Asn Trp Gly Glu Leu Thr Asp Tyr Trp Gly
         115                 120                 125 cag gga acc ctg gtc acc gtc tcc                                     408
Gln Gly Thr Leu Val Thr Val Ser
```

-continued

```
              130                 135

<210> SEQ ID NO 6
<211> LENGTH: 421
<212> TYPE: DNA
<213> ORGANISM: Pan troglodytes
<220> FEATURE:
<221> NAME/KEY: CDS
<222> LOCATION: (1)...(421)

<400> SEQUENCE: 6 atg atg ggg tca acc gcc atc ctc gcc ctc ctc ctg gct gtt ctc caa       48
Met Met Gly Ser Thr Ala Ile Leu Ala Leu Leu Leu Ala Val Leu Gln
 1               5                  10                  15 gga gtc tgt gca gag gtg cag ctg gtg cag tct gga gca gag gtg aaa       96
Gly Val Cys Ala Glu Val Gln Leu Val Gln Ser Gly Ala Glu Val Lys
             20                  25                  30 aag ccc ggg gag tct ctg aag atc tcc tgt aag ggc tct gga tac agt      144
Lys Pro Gly Glu Ser Leu Lys Ile Ser Cys Lys Gly Ser Gly Tyr Ser
         35                  40                  45 ttt acc aac tac tgg atg ggc tgg gtg tgc cag atg ccc ggg aaa ggc      192
Phe Thr Asn Tyr Trp Met Gly Trp Val Cys Gln Met Pro Gly Lys Gly
     50                  55                  60 ccg gag tgc atg ggg atc atc tat cct gat gac tct gat acc aga tac      240
Pro Glu Cys Met Gly Ile Ile Tyr Pro Asp Asp Ser Asp Thr Arg Tyr
 65                  70                  75                  80 agc ccg tcc ttc caa ggc cag gtc acc atc tca gcc gac aag tcc atc      288
Ser Pro Ser Phe Gln Gly Gln Val Thr Ile Ser Ala Asp Lys Ser Ile
                 85                  90                  95 agc acc gcc tac cta caa tgg agc aac ctg aag gcc tcg gac acc gcc      336
Ser Thr Ala Tyr Leu Gln Trp Ser Asn Leu Lys Ala Ser Asp Thr Ala
            100                 105                 110 ata tat tac tgt gcg aga tgt tat ggt tgg act act tgc gaa gct ttt      384
Ile Tyr Tyr Cys Ala Arg Cys Tyr Gly Trp Thr Thr Cys Glu Ala Phe
        115                 120                 125 gat atc tgg ggc caa ggg aca atg gtc acc gtc tct t                     421
Asp Ile Trp Gly Gln Gly Thr Met Val Thr Val Ser
    130                 135                 140

<210> SEQ ID NO 7
<211> LENGTH: 417
<212> TYPE: DNA
<213> ORGANISM: Pan troglodytes
<220> FEATURE:
<221> NAME/KEY: CDS
<222> LOCATION: (1)...(417)

<400> SEQUENCE: 7 ttg tgg ttc ttc ctt ctc ctg gtg gca gct ccc aga tgg gtc ctg tcc       48
Leu Trp Phe Phe Leu Leu Leu Val Ala Ala Pro Arg Trp Val Leu Ser
 1               5                  10                  15 cag ctg cag ctg cag gag tcg ggc cca gga ctg gtg aag cct tca cag       96
Gln Leu Gln Leu Gln Glu Ser Gly Pro Gly Leu Val Lys Pro Ser Gln
             20                  25                  30 acc ctg tcc ctc acc tgc act gtc tct ggt ggc tcc atc agc agt ggt      144
Thr Leu Ser Leu Thr Cys Thr Val Ser Gly Gly Ser Ile Ser Ser Gly
         35                  40                  45 agt tac tac tgg agt tgg atc cgg cag ccc gcc ggg aag cga ctg gag      192
Ser Tyr Tyr Trp Ser Trp Ile Arg Gln Pro Ala Gly Lys Arg Leu Glu
     50                  55                  60 tgg att ggg tat att tat tat agt ggg agt acc tac tac aac cca tcc      240
Trp Ile Gly Tyr Ile Tyr Tyr Ser Gly Ser Thr Tyr Tyr Asn Pro Ser
 65                  70                  75                  80
```

```
ctc aag agt cga gtc acc ata tca gta gac acg tcc aag aac cag ttc      288
Leu Lys Ser Arg Val Thr Ile Ser Val Asp Thr Ser Lys Asn Gln Phe
                85                  90                  95 tcc ctg aag ctg agc tct gtg acc gcc gca gac acg gcc gtc tat tac      336
Ser Leu Lys Leu Ser Ser Val Thr Ala Ala Asp Thr Ala Val Tyr Tyr
            100                 105                 110 tgt gcg aga tct ccc caa aac gta tta caa tct ttg gac tgc ttc gac      384
Cys Ala Arg Ser Pro Gln Asn Val Leu Gln Ser Leu Asp Cys Phe Asp
        115                 120                 125 ccc tgg ggc cag gga acc ctg gtc acc gtc tcc                          417
Pro Trp Gly Gln Gly Thr Leu Val Thr Val Ser
    130                 135
```

<210> SEQ ID NO 8
<211> LENGTH: 369
<212> TYPE: DNA
<213> ORGANISM: Pan troglodytes
<220> FEATURE:
<221> NAME/KEY: CDS
<222> LOCATION: (1)...(369)

<400> SEQUENCE: 8

```
gtc cag tcc cag gtc cag ctg gtg cag tcc ggg gct gag gtg aag aag       48
Val Gln Ser Gln Val Gln Leu Val Gln Ser Gly Ala Glu Val Lys Lys
 1               5                  10                  15 cct ggg tcc tca gtg aag gtc tcc tgc aag gtt tcc gga ggc acc ttc       96
Pro Gly Ser Ser Val Lys Val Ser Cys Lys Val Ser Gly Gly Thr Phe
                20                  25                  30 agc acc tat ggt ttc agc tgg gtg cgg cag gcc cct gga caa ggg ctt      144
Ser Thr Tyr Gly Phe Ser Trp Val Arg Gln Ala Pro Gly Gln Gly Leu
            35                  40                  45 gag tgg atg gga atg atc atc cct atc gtt ggc aca gta aag tac gca      192
Glu Trp Met Gly Met Ile Ile Pro Ile Val Gly Thr Val Lys Tyr Ala
        50                  55                  60 cag agg ttc cag ggc aga gtc tca att aat gcg gac aca tcc acg aat      240
Gln Arg Phe Gln Gly Arg Val Ser Ile Asn Ala Asp Thr Ser Thr Asn
 65                  70                  75                  80 ata gcc tac atg gag ctg acc agc ctg aga tct gag gac acg gcc gtc      288
Ile Ala Tyr Met Glu Leu Thr Ser Leu Arg Ser Glu Asp Thr Ala Val
                85                  90                  95 tat tac tgt gcg aca gat ctg acg gtg act act aat gat gca ttt gat      336
Tyr Tyr Cys Ala Thr Asp Leu Thr Val Thr Thr Asn Asp Ala Phe Asp
                100                 105                 110 atc tgg ggc caa ggg aca atg gtc acc gtc tct                          369
Ile Trp Gly Gln Gly Thr Met Val Thr Val Ser
        115                 120
```

<210> SEQ ID NO 9
<211> LENGTH: 423
<212> TYPE: DNA
<213> ORGANISM: Pan troglodytes
<220> FEATURE:
<221> NAME/KEY: CDS
<222> LOCATION: (1)...(423)

<400> SEQUENCE: 9

```
atg gag ttt ggg ctg agc tgg ctt ttt ctt gtg gct att tta aaa ggt       48
Met Glu Phe Gly Leu Ser Trp Leu Phe Leu Val Ala Ile Leu Lys Gly
 1               5                  10                  15 gtc cag tgt gag gtg cag ctg gtg gag tct ggg gaa ggc ttg gta aag       96
Val Gln Cys Glu Val Gln Leu Val Glu Ser Gly Glu Gly Leu Val Lys
                20                  25                  30
```

```
cct ggg ggt tcc ctg aga ctc tcg tgt gca gcc tct gga ttc acc ttc        144
Pro Gly Gly Ser Leu Arg Leu Ser Cys Ala Ala Ser Gly Phe Thr Phe
        35                  40                  45 agt agt ttt ctt atg ttc tgg gtc cgc cag gct cca gaa aag ggg ctg        192
Ser Ser Phe Leu Met Phe Trp Val Arg Gln Ala Pro Glu Lys Gly Leu
50                  55                  60 gag tgg gtc tca act att gat gtt agt ggt ggt aat atg tgg tac cga        240
Glu Trp Val Ser Thr Ile Asp Val Ser Gly Gly Asn Met Trp Tyr Arg
65                  70                  75                  80 gac tct gtc aag ggc cga ttc acc atg tcc aga gac aat tcc aag aac        288
Asp Ser Val Lys Gly Arg Phe Thr Met Ser Arg Asp Asn Ser Lys Asn
                85                  90                  95 aca ctg tat ctg caa atg acc agc ctg aga gcc gac gac acg gcc gtt        336
Thr Leu Tyr Leu Gln Met Thr Ser Leu Arg Ala Asp Asp Thr Ala Val
            100                 105                 110 tac tat tgt gcg aga gag gga cga gac cct agc ggc act tgg gga tac        384
Tyr Tyr Cys Ala Arg Glu Gly Arg Asp Pro Ser Gly Thr Trp Gly Tyr
        115                 120                 125 ttt gac tac tgg ggc cag gga atc ctg gtc acc gtc tcc                    423
Phe Asp Tyr Trp Gly Gln Gly Ile Leu Val Thr Val Ser
130                 135                 140

<210> SEQ ID NO 10
<211> LENGTH: 97
<212> TYPE: PRT
<213> ORGANISM: Pan troglodytes
<220> FEATURE:
<221> NAME/KEY: DOMAIN
<222> LOCATION: (31)...(37)
<223> OTHER INFORMATION: CDRI
<221> NAME/KEY: DOMAIN
<222> LOCATION: (52)...(67)
<223> OTHER INFORMATION: CDRII

<400> SEQUENCE: 10

Gln Val Gln Leu Gln Glu Ser Gly Pro Gly Leu Val Lys Pro Ser Gln
1               5                   10                  15

Thr Leu Ser Leu Thr Cys Ala Val Ser Gly Gly Ser Ile Thr Ser Ala
            20                  25                  30

Tyr Tyr Tyr Trp Ser Trp Ile Arg Gln Ser Pro Gly Lys Gly Leu Glu
        35                  40                  45

Trp Ile Gly Ser Ile Tyr Tyr Ser Gly Thr Ile Phe Ser Asn Pro Ser
    50                  55                  60

Leu Lys Ser Arg Val Ala Met Ser Val Gly Thr Ser Lys Thr Gln Phe
65                  70                  75                  80

Ser Leu Ser Leu Ser Ser Val Thr Ala Ala Asp Thr Ala Val Tyr Tyr
                85                  90                  95

Cys

<210> SEQ ID NO 11
<211> LENGTH: 96
<212> TYPE: PRT
<213> ORGANISM: Pan troglodytes
<220> FEATURE:
<221> NAME/KEY: DOMAIN
<222> LOCATION: (31)...(37)
<223> OTHER INFORMATION: CDRI
<221> NAME/KEY: DOMAIN
<222> LOCATION: (52)...(67)
<223> OTHER INFORMATION: CDRII

<400> SEQUENCE: 11

Gln Val Gln Leu Gln Glu Ser Gly Pro Gly Leu Val Lys Pro Ser Gln
```

-continued

```
                1               5              10              15
Thr Leu Ser Leu Thr Cys Gly Val Ser Gly Ala Ser Ile Asn Ser Gly
                20                  25                  30

Val His Tyr Trp Ala Trp Ile Arg Gln Pro Ala Gly Lys Gly Leu Glu
            35                  40                  45

Trp Ile Gly Asn Ile Tyr His Ser Gly Ser Ala Tyr Tyr Thr Pro Ser
        50                  55                  60

Leu Glu Ser Arg Val Ser Met Ser Ile Glu Thr Ser Lys Ser Gln Phe
65                  70                  75                  80

Phe Leu Asn Leu Asn Ser Leu Thr Ala Asp Thr Ala Ile Tyr Tyr Cys
                85                  90                  95
```

<210> SEQ ID NO 12
<211> LENGTH: 96
<212> TYPE: PRT
<213> ORGANISM: Pan troglodytes
<220> FEATURE:
<221> NAME/KEY: DOMAIN
<222> LOCATION: (31)...(35)
<223> OTHER INFORMATION: CDRI
<221> NAME/KEY: DOMAIN
<222> LOCATION: (50)...(66)
<223> OTHER INFORMATION: CDRII

<400> SEQUENCE: 12

```
Asp Val Gln Leu Val Gln Ser Gly Ala Glu Val Lys Lys Pro Gly Glu
 1               5                  10                  15

Ser Leu Lys Ile Ser Cys Lys Val Ser Gly Asn Glu Phe Thr Asn Tyr
                20                  25                  30

Trp Ile Ala Trp Val Arg Gln Met Ser Gly Lys Gly Leu Glu Trp Met
            35                  40                  45

Gly Ser Ile Tyr Pro Gly Asp Ser Asp Thr Arg Tyr Asn Pro Ser Phe
        50                  55                  60

Gln Gly Gln Val Thr Phe Ser Ala Asp Lys Ser Ile Thr Thr Ala Tyr
65                  70                  75                  80

Leu Gln Trp Ser Ser Leu Glu Ala Ser Asp Thr Ala Met Tyr Tyr Cys
                85                  90                  95
```

<210> SEQ ID NO 13
<211> LENGTH: 96
<212> TYPE: PRT
<213> ORGANISM: Pan troglodytes
<220> FEATURE:
<221> NAME/KEY: DOMAIN
<222> LOCATION: (31)...(35)
<223> OTHER INFORMATION: CDRI
<221> NAME/KEY: DOMAIN
<222> LOCATION: (50)...(66)
<223> OTHER INFORMATION: CDRII

<400> SEQUENCE: 13

```
Asp Val Gln Leu Val Gln Ser Gly Ala Glu Val Lys Lys Pro Gly Glu
 1               5                  10                  15

Ser Leu Lys Ile Ser Cys Lys Val Ser Gly Asn Glu Phe Thr Asn Tyr
                20                  25                  30

Trp Ile Ala Trp Val Arg Gln Met Ser Gly Lys Gly Leu Glu Trp Met
            35                  40                  45

Gly Ser Ile Tyr Pro Gly Asp Ser Asp Thr Arg Tyr Asn Pro Ser Phe
        50                  55                  60

Gln Gly Gln Val Thr Phe Ser Ala Asp Lys Ser Ile Thr Thr Ala Tyr
65                  70                  75                  80
```

```
Leu Gln Trp Ser Ser Leu Glu Ala Ser Asp Thr Ala Met Tyr Tyr Cys
                85                  90                  95

<210> SEQ ID NO 14
<211> LENGTH: 96
<212> TYPE: PRT
<213> ORGANISM: Pan troglodytes
<220> FEATURE:
<221> NAME/KEY: DOMAIN
<222> LOCATION: (31)...(35)
<223> OTHER INFORMATION: CDRI
<221> NAME/KEY: DOMAIN
<222> LOCATION: (50)...(66)
<223> OTHER INFORMATION: CDRII

<400> SEQUENCE: 14

Glu Val Gln Leu Val Glu Ser Gly Gly Gly Leu Val Gln Pro Gly Gly
 1               5                  10                  15

Ser Leu Thr Leu Ser Cys Ala Ala Ser Gly Phe Thr Phe Ser Arg Ser
                20                  25                  30

Gly Met His Trp Val Arg Gln Ala Pro Gly Lys Gly Leu Gly Trp Leu
                35                  40                  45

Ala Tyr Ile Asp Tyr Gly Ser Ile Phe Ile Tyr Tyr Ser Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Phe Tyr Tyr Cys
                85                  90                  95

<210> SEQ ID NO 15
<211> LENGTH: 96
<212> TYPE: PRT
<213> ORGANISM: Pan troglodytes
<220> FEATURE:
<221> NAME/KEY: DOMAIN
<222> LOCATION: (31)...(35)
<223> OTHER INFORMATION: CDRI
<221> NAME/KEY: DOMAIN
<222> LOCATION: (50)...(66)
<223> OTHER INFORMATION: CDRII

<400> SEQUENCE: 15

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
                20                  25                  30

Trp Met Gly Trp Val Cys Gln Met Pro Gly Lys Gly Pro Glu Cys Met
                35                  40                  45

Gly Ile Ile Tyr Pro Asp Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Asn Leu Lys Ala Ser Asp Thr Ala Ile Tyr Tyr Cys
                85                  90                  95

<210> SEQ ID NO 16
<211> LENGTH: 97
<212> TYPE: PRT
<213> ORGANISM: Pan troglodytes
<220> FEATURE:
<221> NAME/KEY: DOMAIN
<222> LOCATION: (31)...(37)
<223> OTHER INFORMATION: CDRI
```

```
<221> NAME/KEY: DOMAIN
<222> LOCATION: (52)...(67)
<223> OTHER INFORMATION: CDRII

<400> SEQUENCE: 16
```

Gln Leu Gln Leu Gln Glu Ser Gly Pro Gly Leu Val Lys Pro Ser Gln
 1               5                  10                  15

Thr Leu Ser Leu Thr Cys Thr Val Ser Gly Ser Ile Ser Ser Gly
            20                  25                  30

Ser Tyr Tyr Trp Ser Trp Ile Arg Gln Pro Ala Gly Lys Arg Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys

```
<210> SEQ ID NO 17
<211> LENGTH: 96
<212> TYPE: PRT
<213> ORGANISM: Pan troglodytes
<220> FEATURE:
<221> NAME/KEY: DOMAIN
<222> LOCATION: (31)...(35)
<223> OTHER INFORMATION: CDRI
<221> NAME/KEY: DOMAIN
<222> LOCATION: (50)...(66)
<223> OTHER INFORMATION: CDRII

<400> SEQUENCE: 17
```

Gln Val Gln Leu Val Gln Ser Gly Ala Glu Val Lys Lys Pro Gly Ser
 1               5                  10                  15

Ser Val Lys Val Ser Cys Lys Val Ser Gly Gly Thr Phe Ser Thr Tyr
            20                  25                  30

Gly Phe Ser Trp Val Arg Gln Ala Pro Gly Gln Gly Leu Glu Trp Met
            35                  40                  45

Gly Met Ile Ile Pro Ile Val Gly Thr Val Lys Tyr Ala Gln Arg Phe
 50                  55                  60

Gln Gly Arg Val Ser Ile Asn Ala Asp Thr Ser Thr Asn Ile Ala Tyr
65                  70                  75                  80

Met Glu Leu Thr Ser Leu Arg Ser Glu Asp Thr Ala Val Tyr Tyr Cys
            85                  90                  95

```
<210> SEQ ID NO 18
<211> LENGTH: 96
<212> TYPE: PRT
<213> ORGANISM: Pan troglodytes
<220> FEATURE:
<221> NAME/KEY: DOMAIN
<222> LOCATION: (31)...(35)
<223> OTHER INFORMATION: CDRI
<221> NAME/KEY: DOMAIN
<222> LOCATION: (50)...(66)
<223> OTHER INFORMATION: CDRII

<400> SEQUENCE: 18
```

Glu Val Gln Leu Val Glu Ser Gly Glu Gly Leu Val Lys Pro Gly Gly
 1               5                  10                  15

Ser Leu Arg Leu Ser Cys Ala Ala Ser Gly Phe Thr Phe Ser Ser Phe
            20                  25                  30

```
Leu Met Phe Trp Val Arg Gln Ala Pro Glu Lys Gly Leu Glu Trp Val
            35                  40                  45

Ser Thr Ile Asp Val Ser Gly Gly Asn Met Trp Tyr Arg Asp Ser Val
        50                  55                  60

Lys Gly Arg Phe Thr Met Ser Arg Asp Asn Ser Lys Asn Thr Leu Tyr
65                  70                  75                  80

Leu Gln Met Thr Ser Leu Arg Ala Asp Asp Thr Ala Val Tyr Tyr Cys
                85                  90                  95

<210> SEQ ID NO 19
<211> LENGTH: 381
<212> TYPE: DNA
<213> ORGANISM: Pan troglodytes
<220> FEATURE:
<221> NAME/KEY: CDS
<222> LOCATION: (1)...(381)

<400> SEQUENCE: 19 atg agg gtc cct gct cag ctc ctg ggg ctc ctg ctg ctc tgg ctc tca      48
Met Arg Val Pro Ala Gln Leu Leu Gly Leu Leu Leu Leu Trp Leu Ser
 1               5                  10                  15 ggt gcc aga tgt gac atc cag atg acc cag ttt cca tcc tcc ctg tct      96
Gly Ala Arg Cys Asp Ile Gln Met Thr Gln Phe Pro Ser Ser Leu Ser
            20                  25                  30 gca tct gta gga gac aga gtc acc atc act tgc cag tca agt cag agc     144
Ala Ser Val Gly Asp Arg Val Thr Ile Thr Cys Gln Ser Ser Gln Ser
        35                  40                  45 att tac aac tgc ttg agt tgg tat cag cag aaa cca ggg aag gcc cct     192
Ile Tyr Asn Cys Leu Ser Trp Tyr Gln Gln Lys Pro Gly Lys Ala Pro
    50                  55                  60 aca ctc cta atc tat ggt gca ttc acc ttg aat agt ggg gtc cca tca     240
Thr Leu Leu Ile Tyr Gly Ala Phe Thr Leu Asn Ser Gly Val Pro Ser
65                  70                  75                  80 aga ttc agt ggc agt gga tct ggc aca gat ttc act ctc acc atc agc     288
Arg Phe Ser Gly Ser Gly Ser Gly Thr Asp Phe Thr Leu Thr Ile Ser
                85                  90                  95 aat ctg caa cct gaa gat ttt gca aca tat tac tgt cag cgt ggt tac     336
Asn Leu Gln Pro Glu Asp Phe Ala Thr Tyr Tyr Cys Gln Arg Gly Tyr
            100                 105                 110 ggc aca cag ctc act ttc ggt gga ggg acc aag gtg gag atc aag         381
Gly Thr Gln Leu Thr Phe Gly Gly Gly Thr Lys Val Glu Ile Lys
        115                 120                 125

<210> SEQ ID NO 20
<211> LENGTH: 384
<212> TYPE: DNA
<213> ORGANISM: Pan troglodytes
<220> FEATURE:
<221> NAME/KEY: CDS
<222> LOCATION: (1)...(384)

<400> SEQUENCE: 20 atg gac atg agg gtc ccc gct cag ctc ctg ggg ctc ctg ctg ctc tgg      48
Met Asp Met Arg Val Pro Ala Gln Leu Leu Gly Leu Leu Leu Leu Trp
 1               5                  10                  15 ctc cca ggt acc aga tgt gac atc cag atg acc cag tct cca tcc tcc      96
Leu Pro Gly Thr Arg Cys Asp Ile Gln Met Thr Gln Ser Pro Ser Ser
            20                  25                  30 ctg tct gca tct gta gga gac aga gtc acc atc act tgc cgg gcc agt     144
Leu Ser Ala Ser Val Gly Asp Arg Val Thr Ile Thr Cys Arg Ala Ser
        35                  40                  45
```

```
cag ggc att agc aat tat tta gcc tgg tat cag cag aaa cca ggg aaa        192
Gln Gly Ile Ser Asn Tyr Leu Ala Trp Tyr Gln Gln Lys Pro Gly Lys
     50                  55                  60 gcc cct aag ctc ctc atc tat tat gca tcc aga ttg gaa agt ggg gtc        240
Ala Pro Lys Leu Leu Ile Tyr Tyr Ala Ser Arg Leu Glu Ser Gly Val
 65                  70                  75                  80 cca tca agg ttc agc ggc agt gga tct ggg acg gat tac act ctc acc        288
Pro Ser Arg Phe Ser Gly Ser Gly Ser Gly Thr Asp Tyr Thr Leu Thr
                 85                  90                  95 atc agc agc ctg cag cct gaa gat ttt gca act tat tac tgt caa cag        336
Ile Ser Ser Leu Gln Pro Glu Asp Phe Ala Thr Tyr Tyr Cys Gln Gln
            100                 105                 110 tat aac agt aac ccc ttt tcg gtg gag gga cca agg tgg aga tca aac        384
Tyr Asn Ser Asn Pro Phe Ser Val Glu Gly Pro Arg Trp Arg Ser Asn
                115                 120                 125

<210> SEQ ID NO 21
<211> LENGTH: 384
<212> TYPE: DNA
<213> ORGANISM: Pan troglodytes
<220> FEATURE:
<221> NAME/KEY: CDS
<222> LOCATION: (1)...(384)

<400> SEQUENCE: 21 atg tcg cca tca caa ctc att ggg ttt ctg ctg ctc tgg gtt cca gcc         48
Met Ser Pro Ser Gln Leu Ile Gly Phe Leu Leu Leu Trp Val Pro Ala
  1               5                  10                  15 tcc agg ggt gaa att gtg ctg act cag tct cca gac ttt cag tct gtg         96
Ser Arg Gly Glu Ile Val Leu Thr Gln Ser Pro Asp Phe Gln Ser Val
                 20                  25                  30 cct cca aag gag aaa gtc acc atc acc tgc cgg gcc agt cag agc att        144
Pro Pro Lys Glu Lys Val Thr Ile Thr Cys Arg Ala Ser Gln Ser Ile
             35                  40                  45 ggt agt agc tta cac tgg tac cag cag aaa cca ggt cag tct cca aag        192
Gly Ser Ser Leu His Trp Tyr Gln Gln Lys Pro Gly Gln Ser Pro Lys
     50                  55                  60 ctc ctc atc aag tat gct tcc cag tcc atc tca ggg gtc ccc tcg agg        240
Leu Leu Ile Lys Tyr Ala Ser Gln Ser Ile Ser Gly Val Pro Ser Arg
 65                  70                  75                  80 ttc agt ggc agt gga tct ggg aca gat ttc acc ctc acc atc aat agc        288
Phe Ser Gly Ser Gly Ser Gly Thr Asp Phe Thr Leu Thr Ile Asn Ser
                 85                  90                  95 ctg gaa gct gaa gat gct gca acg tat tac tgt cag caa agt agt aat        336
Leu Glu Ala Glu Asp Ala Ala Thr Tyr Tyr Cys Gln Gln Ser Ser Asn
            100                 105                 110 tta cct cat acg ctc act ttc ggt gga ggg acc aag gtg gag atc aaa        384
Leu Pro His Thr Leu Thr Phe Gly Gly Gly Thr Lys Val Glu Ile Lys
                115                 120                 125

<210> SEQ ID NO 22
<211> LENGTH: 372
<212> TYPE: DNA
<213> ORGANISM: Pan troglodytes
<220> FEATURE:
<221> NAME/KEY: CDS
<222> LOCATION: (1)...(372)

<400> SEQUENCE: 22 gtc cct gct cag ctc ctg ggg ctc ctg ctc tgg ctc tca ggt gcc             48
Val Pro Ala Gln Leu Leu Gly Leu Leu Leu Trp Leu Ser Gly Ala
  1               5                  10                  15 aga tgt gac atc cag atg acc cag tct cca tcc tcc ctg tct gca tct        96
Arg Cys Asp Ile Gln Met Thr Gln Ser Pro Ser Ser Leu Ser Ala Ser
```

```
                Arg Cys Asp Ile Gln Met Thr Gln Ser Pro Ser Ser Leu Ser Ala Ser
                            20                  25                  30 gta gga gac aga gtc acc atc act tgc cag gca agt cag agc att agc      144
Val Gly Asp Arg Val Thr Ile Thr Cys Gln Ala Ser Gln Ser Ile Ser
         35                  40                  45 aac tat ttg agt tgg tat cag cag aaa cca ggg aaa gcc cct aag ctc      192
Asn Tyr Leu Ser Trp Tyr Gln Gln Lys Pro Gly Lys Ala Pro Lys Leu
 50                  55                  60 ctg atc tat gat gca tcc act ttg caa agt ggg gtc cca tca agg ttc      240
Leu Ile Tyr Asp Ala Ser Thr Leu Gln Ser Gly Val Pro Ser Arg Phe
 65                  70                  75                  80 agt ggc agt gga tct ggg aca gat ttc act ctc acc atc agc agt ctg      288
Ser Gly Ser Gly Ser Gly Thr Asp Phe Thr Leu Thr Ile Ser Ser Leu
                 85                  90                  95 caa cct gaa gat ttt gca aca tat tac tgt cag cgt ggt tac ggt aca      336
Gln Pro Glu Asp Phe Ala Thr Tyr Tyr Cys Gln Arg Gly Tyr Gly Thr
            100                 105                 110 ctc act ttc ggt gga ggg acc aag gtg gag atc aaa                      372
Leu Thr Phe Gly Gly Gly Thr Lys Val Glu Ile Lys
        115                 120

<210> SEQ ID NO 23
<211> LENGTH: 384
<212> TYPE: DNA
<213> ORGANISM: Pan troglodytes
<220> FEATURE:
<221> NAME/KEY: CDS
<222> LOCATION: (1)...(384)

<400> SEQUENCE: 23 atg gaa gcc cca gcg cag ctt ctc ttc ctc ctg cta ctc tgg ctc cca       48
Met Glu Ala Pro Ala Gln Leu Leu Phe Leu Leu Leu Leu Trp Leu Pro
  1               5                  10                  15 gat acc acc gga gaa ata gtg ttg acg cag tct cca gcc acc ctg tct       96
Asp Thr Thr Gly Glu Ile Val Leu Thr Gln Ser Pro Ala Thr Leu Ser
             20                  25                  30 ttg tct cca ggg gaa aga gcc acc ctc tcc tgc agg gcc agt cag agt      144
Leu Ser Pro Gly Glu Arg Ala Thr Leu Ser Cys Arg Ala Ser Gln Ser
         35                  40                  45 gtt agc agg tac tta gcc tgg tac cag cag aaa cct ggc cag gct ccc      192
Val Ser Arg Tyr Leu Ala Trp Tyr Gln Gln Lys Pro Gly Gln Ala Pro
 50                  55                  60 agg ctc ctc atc tat ggt gca tcc aac agg gcc act ggc atc cca gcc      240
Arg Leu Leu Ile Tyr Gly Ala Ser Asn Arg Ala Thr Gly Ile Pro Ala
 65                  70                  75                  80 agg ttc agt ggc agt ggg tct agg aca gac ttc act ctc acc atc agc      288
Arg Phe Ser Gly Ser Gly Ser Arg Thr Asp Phe Thr Leu Thr Ile Ser
                 85                  90                  95 agc gtg gag cct gaa gat ttt gca gtt tat tac tgt cag cag tat aat      336
Ser Val Glu Pro Glu Asp Phe Ala Val Tyr Tyr Cys Gln Gln Tyr Asn
            100                 105                 110 aac cag cct ctg atc gcc ttc ggc caa ggg aca cga ctg gag att aaa      384
Asn Gln Pro Leu Ile Ala Phe Gly Gln Gly Thr Arg Leu Glu Ile Lys
        115                 120                 125

<210> SEQ ID NO 24
<211> LENGTH: 387
<212> TYPE: DNA
<213> ORGANISM: Pan troglodytes
<220> FEATURE:
<221> NAME/KEY: CDS
<222> LOCATION: (1)...(387)
```

<400> SEQUENCE: 24

```
atg gac atg agg gtc ccc gct cag ctc ctg ggg ctc ctg ctg ctc tgg      48
Met Asp Met Arg Val Pro Ala Gln Leu Leu Gly Leu Leu Leu Leu Trp
 1               5                  10                  15 ttc cca ggt gcc aaa tgt gac atc cag atg acc cag tct cct tcc acc      96
Phe Pro Gly Ala Lys Cys Asp Ile Gln Met Thr Gln Ser Pro Ser Thr
                 20                  25                  30 ctg tct gcc tcc ata gga gac aga gtc acc atc act tgt cgg gct agt     144
Leu Ser Ala Ser Ile Gly Asp Arg Val Thr Ile Thr Cys Arg Ala Ser
             35                  40                  45 cag ggc atc tat aat tat ttg aat tgg tat cag caa aaa cca ggg aga     192
Gln Gly Ile Tyr Asn Tyr Leu Asn Trp Tyr Gln Gln Lys Pro Gly Arg
         50                  55                  60 gcc cct gga ctc ctc atc ttt ggt gcc agg aat ttg gag act ggg gtc     240
Ala Pro Gly Leu Leu Ile Phe Gly Ala Arg Asn Leu Glu Thr Gly Val
 65                  70                  75                  80 cca tca aca ttc agc ggc agt ggt tcc ggg aca cac ttc act ctc acc     288
Pro Ser Thr Phe Ser Gly Ser Gly Ser Gly Thr His Phe Thr Leu Thr
                 85                  90                  95 atc agc agc ctg cag cct ggt gat ttt gcg act tat tac tgt cag caa     336
Ile Ser Ser Leu Gln Pro Gly Asp Phe Ala Thr Tyr Tyr Cys Gln Gln
            100                 105                 110 tat tat act acc ccg tat act ttt ggc cag ggg acc aag ctg gag atc     384
Tyr Tyr Thr Thr Pro Tyr Thr Phe Gly Gln Gly Thr Lys Leu Glu Ile
        115                 120                 125 aaa                                                                  387
```

<210> SEQ ID NO 25
<211> LENGTH: 387
<212> TYPE: DNA
<213> ORGANISM: Pan troglodytes
<220> FEATURE:
<221> NAME/KEY: CDS
<222> LOCATION: (1)...(387)

<400> SEQUENCE: 25

```
atg gac atg agg gtc ccc gct cag ctc ctg ggg ctc ctg ctg ctc tgt      48
Met Asp Met Arg Val Pro Ala Gln Leu Leu Gly Leu Leu Leu Leu Cys
 1               5                  10                  15 ttc cca ggt gcc aga tgt gac atc cag atg acc cag tct cca tcc tca      96
Phe Pro Gly Ala Arg Cys Asp Ile Gln Met Thr Gln Ser Pro Ser Ser
                 20                  25                  30 ctg tct gct tct gta gga gac aga gtc acc atc tct tgt cgg gcg agt     144
Leu Ser Ala Ser Val Gly Asp Arg Val Thr Ile Ser Cys Arg Ala Ser
             35                  40                  45 ctg gat att agc acc tgg tta gcc tgg tat cag cag aaa cca ggg aaa     192
Leu Asp Ile Ser Thr Trp Leu Ala Trp Tyr Gln Gln Lys Pro Gly Lys
         50                  55                  60 gcc cct aag ccc ctg atc tat gct gca tcc act ttg cca agt ggg gtc     240
Ala Pro Lys Pro Leu Ile Tyr Ala Ala Ser Thr Leu Pro Ser Gly Val
 65                  70                  75                  80 cca tcg agg ttc agc ggc agt gga tct ggg aca gat ttc act ctc acc     288
Pro Ser Arg Phe Ser Gly Ser Gly Ser Gly Thr Asp Phe Thr Leu Thr
                 85                  90                  95 atc agc agc ctg cag cct gaa gat tct gca act tat tac tgc cga caa     336
Ile Ser Ser Leu Gln Pro Glu Asp Ser Ala Thr Tyr Tyr Cys Arg Gln
            100                 105                 110 tat aat agt tat ccg ctc act ttc ggt gga ggg acc aag gtg gag atc     384
Tyr Asn Ser Tyr Pro Leu Thr Phe Gly Gly Gly Thr Lys Val Glu Ile
        115                 120                 125
``` aag                                                                      387

<210> SEQ ID NO 26
<211> LENGTH: 372
<212> TYPE: DNA
<213> ORGANISM: Pan troglodytes
<220> FEATURE:
<221> NAME/KEY: CDS
<222> LOCATION: (1)...(372)

<400> SEQUENCE: 26

```
tct act cag ctc ctg ggg ctc ctg ctg ctc tgg ctc cca ggt gcc aaa       48
Ser Thr Gln Leu Leu Gly Leu Leu Leu Leu Trp Leu Pro Gly Ala Lys
  1               5                  10                  15 tgt gac atc cag atg acc cag tct cct tcc acc ctg tct gca tct gta       96
Cys Asp Ile Gln Met Thr Gln Ser Pro Ser Thr Leu Ser Ala Ser Val
             20                  25                  30 gga gac aga gtc acc atc act tgc cgg gcc agt cag ggt att agt agc      144
Gly Asp Arg Val Thr Ile Thr Cys Arg Ala Ser Gln Gly Ile Ser Ser
         35                  40                  45 tgg tta gcc tgg tat cag cag aaa cca ggg aaa gcc cct aag ctc ctg      192
Trp Leu Ala Trp Tyr Gln Gln Lys Pro Gly Lys Ala Pro Lys Leu Leu
     50                  55                  60 atc tat aag gca tct agt tta gaa agt ggg gtc cca tca agg ttc agc      240
Ile Tyr Lys Ala Ser Ser Leu Glu Ser Gly Val Pro Ser Arg Phe Ser
 65                  70                  75                  80 ggc agt gga tct ggg aca gaa ttc act ctc acc atc agc agc ctg cag      288
Gly Ser Gly Ser Gly Thr Glu Phe Thr Leu Thr Ile Ser Ser Leu Gln
                 85                  90                  95 cct gat gat ttt gca act tat tac tgc caa cag tat agt agt tac cct      336
Pro Asp Asp Phe Ala Thr Tyr Tyr Cys Gln Gln Tyr Ser Ser Tyr Pro
                100                 105                 110 cga acg ttc ggc caa ggg acc aag ctg gaa atc aaa                      372
Arg Thr Phe Gly Gln Gly Thr Lys Leu Glu Ile Lys
                115                 120
```

<210> SEQ ID NO 27
<211> LENGTH: 387
<212> TYPE: DNA
<213> ORGANISM: Pan troglodytes
<220> FEATURE:
<221> NAME/KEY: CDS
<222> LOCATION: (1)...(387)

<400> SEQUENCE: 27

```
atg gac atg agg gtc ccc gct cag ctc ctg ggg ctc ctg ctg ctc tgg       48
Met Asp Met Arg Val Pro Ala Gln Leu Leu Gly Leu Leu Leu Leu Trp
  1               5                  10                  15 ctc tca ggt acc aga tgt gac atc cag atg acc cag tct cca tcc tcc       96
Leu Ser Gly Thr Arg Cys Asp Ile Gln Met Thr Gln Ser Pro Ser Ser
             20                  25                  30 ctg tct gca tct gta gga gac aga gtc acc atc act tgc cgg gca agt      144
Leu Ser Ala Ser Val Gly Asp Arg Val Thr Ile Thr Cys Arg Ala Ser
         35                  40                  45 cag agc att agc aac tat ttg agt tgg tat cag cag aaa cca ggg aaa      192
Gln Ser Ile Ser Asn Tyr Leu Ser Trp Tyr Gln Gln Lys Pro Gly Lys
     50                  55                  60 gcc cct aag ctc ctg atc tat tat gca tcc act ttg caa agt ggg gtc      240
Ala Pro Lys Leu Leu Ile Tyr Tyr Ala Ser Thr Leu Gln Ser Gly Val
 65                  70                  75                  80 cca tca agg ttc agt ggc agt gga tct ggg aca gat ttc act ctc acc      288
Pro Ser Arg Phe Ser Gly Ser Gly Ser Gly Thr Asp Phe Thr Leu Thr
                 85                  90                  95
```

```
atc agc agt ctg caa cct gaa gat ttt gca act tat tac tgt cag cat      336
Ile Ser Ser Leu Gln Pro Glu Asp Phe Ala Thr Tyr Tyr Cys Gln His
        100                 105                 110 ggt tac ggt aca cat ccc act ttc ggt gga ggg acc aag gtg gag atc      384
Gly Tyr Gly Thr His Pro Thr Phe Gly Gly Gly Thr Lys Val Glu Ile
        115                 120                 125 aaa                                                                   387
```

```
<210> SEQ ID NO 28
<211> LENGTH: 88
<212> TYPE: PRT
<213> ORGANISM: Pan troglodytes
<220> FEATURE:
<221> NAME/KEY: DOMAIN
<222> LOCATION: (24)...(34)
<223> OTHER INFORMATION: CDRI
<221> NAME/KEY: DOMAIN
<222> LOCATION: (50)...(66)
<223> OTHER INFORMATION: CDRII

<400> SEQUENCE: 28
```

Asp Ile Gln Met Thr Gln Phe Pro Ser Ser Leu Ser Ala Ser Val Gly
 1               5                  10                  15

Asp Arg Val Thr Ile Thr Cys Gln Ser Ser Gln Ser Ile Tyr Asn Cys
            20                  25                  30

Leu Ser Trp Tyr Gln Gln Lys Pro Gly Lys Ala Pro Thr Leu Leu Ile
        35                  40                  45

Tyr Gly Ala Phe Thr Leu Asn Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys
                85

```
<210> SEQ ID NO 29
<211> LENGTH: 88
<212> TYPE: PRT
<213> ORGANISM: Pan troglodytes
<220> FEATURE:
<221> NAME/KEY: DOMAIN
<222> LOCATION: (24)...(34)
<223> OTHER INFORMATION: CDRI
<221> NAME/KEY: DOMAIN
<222> LOCATION: (50)...(66)
<223> OTHER INFORMATION: CDRII

<400> SEQUENCE: 29
```

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Tyr Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys
                85

```
<210> SEQ ID NO 30
```

```
<211> LENGTH: 88
<212> TYPE: PRT
<213> ORGANISM: Pan troglodytes
<220> FEATURE:
<221> NAME/KEY: DOMAIN
<222> LOCATION: (24)...(34)
<223> OTHER INFORMATION: CDRI
<221> NAME/KEY: DOMAIN
<222> LOCATION: (50)...(66)
<223> OTHER INFORMATION: CDRII

<400> SEQUENCE: 30
```

Glu Ile Val Leu Thr Gln Ser Pro Asp Phe Gln Ser Val Pro Pro Lys
 1               5                  10                  15

Glu Lys Val Thr Ile Thr Cys Arg Ala Ser Gln Ser Ile Gly Ser Ser
             20                  25                  30

Leu His Trp Tyr Gln Gln Lys Pro Gly Gln Ser Pro Lys Leu Leu Ile
         35                  40                  45

Lys Tyr Ala Ser Gln Ser Ile Ser Gly Val Pro Ser Arg Phe Ser Gly
 50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys
                 85

```
<210> SEQ ID NO 31
<211> LENGTH: 88
<212> TYPE: PRT
<213> ORGANISM: Pan troglodytes
<220> FEATURE:
<221> NAME/KEY: DOMAIN
<222> LOCATION: (24)...(34)
<223> OTHER INFORMATION: CDRI
<221> NAME/KEY: DOMAIN
<222> LOCATION: (50)...(66)
<223> OTHER INFORMATION: CDRII

<400> SEQUENCE: 31
```

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Ile Ser Asn Tyr
             20                  25                  30

Leu Ser Trp Tyr Gln Gln Lys Pro Gly Lys Ala Pro Lys Leu Leu Ile
         35                  40                  45

Tyr Asp Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                 85

```
<210> SEQ ID NO 32
<211> LENGTH: 88
<212> TYPE: PRT
<213> ORGANISM: Pan troglodytes
<220> FEATURE:
<221> NAME/KEY: DOMAIN
<222> LOCATION: (24)...(34)
<223> OTHER INFORMATION: CDRI
<221> NAME/KEY: DOMAIN
<222> LOCATION: (50)...(66)
<223> OTHER INFORMATION: CDRII

<400> SEQUENCE: 32
```

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Arg Tyr
             20                  25                  30

Leu Ala Trp Tyr Gln Gln Lys Pro Gly Gln Ala Pro Arg Leu Leu Ile
         35                  40                  45

Tyr Gly Ala Ser Asn Arg Ala Thr Gly Ile Pro Ala Arg Phe Ser Gly
 50                  55                  60

Ser Gly Ser Arg Thr Asp Phe Thr Leu Thr Ile Ser Ser Val Glu Pro
 65                  70                  75                  80

Glu Asp Phe Ala Val Tyr Tyr Cys
                 85
```

<210> SEQ ID NO 33
<211> LENGTH: 88
<212> TYPE: PRT
<213> ORGANISM: Pan troglodytes
<220> FEATURE:
<221> NAME/KEY: DOMAIN
<222> LOCATION: (24)...(34)
<223> OTHER INFORMATION: CDRI
<221> NAME/KEY: DOMAIN
<222> LOCATION: (50)...(66)
<223> OTHER INFORMATION: CDRII

<400> SEQUENCE: 33

```
Asp Ile Gln Met Thr Gln Ser Pro Ser Thr Leu Ser Ala Ser Ile Gly
  1               5                  10                  15

Asp Arg Val Thr Ile Thr Cys Arg Ala Ser Gln Gly Ile Tyr Asn Tyr
             20                  25                  30

Leu Asn Trp Tyr Gln Gln Lys Pro Gly Arg Ala Pro Gly Leu Leu Ile
         35                  40                  45

Phe Gly Ala Arg Asn Leu Glu Thr Gly Val Pro Ser Thr Phe Ser Gly
 50                  55                  60

Ser Gly Ser Gly Thr His Phe Thr Leu Thr Ile Ser Ser Leu Gln Pro
 65                  70                  75                  80

Gly Asp Phe Ala Thr Tyr Tyr Cys
                 85
```

<210> SEQ ID NO 34
<211> LENGTH: 88
<212> TYPE: PRT
<213> ORGANISM: Pan troglodytes
<220> FEATURE:
<221> NAME/KEY: DOMAIN
<222> LOCATION: (24)...(34)
<223> OTHER INFORMATION: CDRI
<221> NAME/KEY: DOMAIN
<222> LOCATION: (50)...(66)
<223> OTHER INFORMATION: CDRII

<400> SEQUENCE: 34

```
Asp Ile Gln Met Thr Gln Ser Pro Ser Ser Leu Ser Ala Ser Val Gly
  1               5                  10                  15

Asp Arg Val Thr Ile Ser Cys Arg Ala Ser Leu Asp Ile Ser Thr Trp
             20                  25                  30

Leu Ala Trp Tyr Gln Gln Lys Pro Gly Lys Ala Pro Lys Pro Leu Ile
         35                  40                  45

Tyr Ala Ala Ser Thr Leu Pro Ser Gly Val Pro Ser Arg Phe Ser Gly
 50                  55                  60

Ser Gly Ser Gly Thr Asp Phe Thr Leu Thr Ile Ser Ser Leu Gln Pro
```

-continued

```
               65                  70                  75                  80
        Glu Asp Ser Ala Thr Tyr Tyr Cys
                        85

<210> SEQ ID NO 35
<211> LENGTH: 88
<212> TYPE: PRT
<213> ORGANISM: Pan troglodytes
<220> FEATURE:
<221> NAME/KEY: DOMAIN
<222> LOCATION: (24)...(34)
<223> OTHER INFORMATION: CDRI
<221> NAME/KEY: DOMAIN
<222> LOCATION: (50)...(66)
<223> OTHER INFORMATION: CDRII

<400> SEQUENCE: 35

Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys
                 85

<210> SEQ ID NO 36
<211> LENGTH: 88
<212> TYPE: PRT
<213> ORGANISM: Pan troglodytes
<220> FEATURE:
<221> NAME/KEY: DOMAIN
<222> LOCATION: (24)...(34)
<223> OTHER INFORMATION: CDRI
<221> NAME/KEY: DOMAIN
<222> LOCATION: (50)...(66)
<223> OTHER INFORMATION: CDRII

<400> SEQUENCE: 36

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Asn Tyr
                 20                  25                  30

Leu Ser Trp Tyr Gln Gln Lys Pro Gly Lys Ala Pro Lys Leu Leu Ile
             35                  40                  45

Tyr Tyr Ala Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys
                 85

<210> SEQ ID NO 37
<211> LENGTH: 408
<212> TYPE: DNA
<213> ORGANISM: Macaca cynomolgus
<220> FEATURE:
<221> NAME/KEY: CDS
<222> LOCATION: (1)...(408)
```

<400> SEQUENCE: 37

```
atg gag ttt gga ctg agc tgg gtt ttc ctt gtc gct att ttc aaa ggt    48
Met Glu Phe Gly Leu Ser Trp Val Phe Leu Val Ala Ile Phe Lys Gly
 1               5                  10                  15 gtc cag tgt gaa gtg cag ttg gtg gag tct ggg gga ggc ttg gta cag    96
Val Gln Cys Glu Val Gln Leu Val Glu Ser Gly Gly Gly Leu Val Gln
             20                  25                  30 ccg ggg ggg tcc ctg aga ctc gcc tgt gta ggc tct gga ttc gcc ttc   144
Pro Gly Gly Ser Leu Arg Leu Ala Cys Val Gly Ser Gly Phe Ala Phe
         35                  40                  45 aga aac acc agg atg cac tgg att cga cag act cca gga aag agg ctg   192
Arg Asn Thr Arg Met His Trp Ile Arg Gln Thr Pro Gly Lys Arg Leu
     50                  55                  60 gag tgg gtg gcc gac ata aag ttt gat gga agt gat ttt tac tat gta   240
Glu Trp Val Ala Asp Ile Lys Phe Asp Gly Ser Asp Phe Tyr Tyr Val
 65                  70                  75                  80 gac tct gtg aag ggc cga ttc acc atc tcc aga gac aac gcc aag aac   288
Asp Ser Val Lys Gly Arg Phe Thr Ile Ser Arg Asp Asn Ala Lys Asn
                 85                  90                  95 tcc ctc tat ctg gaa atg aac agc ctg aga cct gat gac aca gcc gtc   336
Ser Leu Tyr Leu Glu Met Asn Ser Leu Arg Pro Asp Asp Thr Ala Val
            100                 105                 110 tat ttc tgt gtg aga gaa tac aga gat gga ctg gat gtc tgg ggc cgg   384
Tyr Phe Cys Val Arg Glu Tyr Arg Asp Gly Leu Asp Val Trp Gly Arg
        115                 120                 125 gga gtt ctg gtc acc gtc tcc tca                                   408
Gly Val Leu Val Thr Val Ser Ser
    130                 135
```

<210> SEQ ID NO 38
<211> LENGTH: 381
<212> TYPE: DNA
<213> ORGANISM: Macaca cynomolgus
<220> FEATURE:
<221> NAME/KEY: CDS
<222> LOCATION: (1)...(381)

<400> SEQUENCE: 38

```
gtg aca gct ccc aga tgg gtc ctg tcc cag gtg caa ttg cag gag tcg    48
Val Thr Ala Pro Arg Trp Val Leu Ser Gln Val Gln Leu Gln Glu Ser
 1               5                  10                  15 ggc cca gga ctg gtg aag cct tcg gag acc ctg tcc ctc act tgt act    96
Gly Pro Gly Leu Val Lys Pro Ser Glu Thr Leu Ser Leu Thr Cys Thr
             20                  25                  30 gtc tct ggt gac tcc atc acc act gtc ttc tgg agc tgg ctc cgc cag   144
Val Ser Gly Asp Ser Ile Thr Thr Val Phe Trp Ser Trp Leu Arg Gln
         35                  40                  45 tcg cca ggg att ggg ctg gag tgg att ggg aat ttt gct ggt agt act   192
Ser Pro Gly Ile Gly Leu Glu Trp Ile Gly Asn Phe Ala Gly Ser Thr
     50                  55                  60 ccg gaa acg aac tac aat ccc tcc ctc aag aat cga gcc acc att tca   240
Pro Glu Thr Asn Tyr Asn Pro Ser Leu Lys Asn Arg Ala Thr Ile Ser
 65                  70                  75                  80 aaa gac acg ccc acg aat caa ttt ttc ctg agg ctg acg tct gtg acc   288
Lys Asp Thr Pro Thr Asn Gln Phe Phe Leu Arg Leu Thr Ser Val Thr
                 85                  90                  95 gcc gcg gac acg gcc gtc tac ttc tgt gcg aga gga ggg gga gcc ggc   336
Ala Ala Asp Thr Ala Val Tyr Phe Cys Ala Arg Gly Gly Gly Ala Gly
            100                 105                 110 aac cca ctc act tgg ggc cag gga gtc cag gtc acc gtc tcc tca       381
Asn Pro Leu Thr Trp Gly Gln Gly Val Gln Val Thr Val Ser Ser
```

-continued

```
Asn Pro Leu Thr Trp Gly Gln Gly Val Gln Val Thr Val Ser Ser
        115                 120                 125

<210> SEQ ID NO 39
<211> LENGTH: 417
<212> TYPE: DNA
<213> ORGANISM: Macaca cynomolgus
<220> FEATURE:
<221> NAME/KEY: CDS
<222> LOCATION: (1)...(417)

<400> SEQUENCE: 39 atg ggg tca act gcc atc ctc gcc ctc ctc ctg gct gtt ctc caa gga      48
Met Gly Ser Thr Ala Ile Leu Ala Leu Leu Leu Ala Val Leu Gln Gly
 1               5                  10                  15 gtc tgt gcc gag gtg cat ctg gtg cag tct gga gca cag gtg aaa agg      96
Val Cys Ala Glu Val His Leu Val Gln Ser Gly Ala Gln Val Lys Arg
             20                  25                  30 ccc ggg gaa tct ctg agg atc tcc tgt aag act tct gga tac acc ttt     144
Pro Gly Glu Ser Leu Arg Ile Ser Cys Lys Thr Ser Gly Tyr Thr Phe
         35                  40                  45 acc gac agc tgg atc agc tgg gtg cgc cag atg ccc ggg aaa ggc ctg     192
Thr Asp Ser Trp Ile Ser Trp Val Arg Gln Met Pro Gly Lys Gly Leu
     50                  55                  60 gag tgg atg gga aac atc tat cct ggt gat tct gat tcc aga tac aac     240
Glu Trp Met Gly Asn Ile Tyr Pro Gly Asp Ser Asp Ser Arg Tyr Asn
 65                  70                  75                  80 ccg tcc ttc caa ggc cgc gtc act atc tca gtc gac aag tcc atc agt     288
Pro Ser Phe Gln Gly Arg Val Thr Ile Ser Val Asp Lys Ser Ile Ser
                 85                  90                  95 acc acc tac ctg cag tgg agc agc ctg aag gcc tcg gac act gcc aca     336
Thr Thr Tyr Leu Gln Trp Ser Ser Leu Lys Ala Ser Asp Thr Ala Thr
            100                 105                 110 tat tac tgt gcg aag ata gat agc aac tac tac agc cgg ttc gaa gtc     384
Tyr Tyr Cys Ala Lys Ile Asp Ser Asn Tyr Tyr Ser Arg Phe Glu Val
        115                 120                 125 tgg ggc ccc gga gtc atg gtc acc gtc tcc tca                         417
Trp Gly Pro Gly Val Met Val Thr Val Ser Ser
    130                 135

<210> SEQ ID NO 40
<211> LENGTH: 423
<212> TYPE: DNA
<213> ORGANISM: Macaca cynomolgus
<220> FEATURE:
<221> NAME/KEY: CDS
<222> LOCATION: (1)...(423)

<400> SEQUENCE: 40 atg aag cac ctg tgg ttc ttc ctc ctc ctg gtg gca gct cct aga tgg      48
Met Lys His Leu Trp Phe Phe Leu Leu Leu Val Ala Ala Pro Arg Trp
 1               5                  10                  15 gtc ctg tcc cag gtg cag ttg cag gag tcg ggc cca gga gtg gtg aag      96
Val Leu Ser Gln Val Gln Leu Gln Glu Ser Gly Pro Gly Val Val Lys
             20                  25                  30 cct tcg gag acc ctg tcc ctc acc tgc act gtc tct ggt ggc tcc ttc     144
Pro Ser Glu Thr Leu Ser Leu Thr Cys Thr Val Ser Gly Gly Ser Phe
         35                  40                  45 agt act tac tac tgg aat tgg atc cgc cag ccc cca ggg aag gga ctg     192
Ser Thr Tyr Tyr Trp Asn Trp Ile Arg Gln Pro Pro Gly Lys Gly Leu
     50                  55                  60 gag tgg att gga tat atc ggt ggt ggt ggt ggt cgc ccc aac tac aat     240
Glu Trp Ile Gly Tyr Ile Gly Gly Gly Gly Gly Arg Pro Asn Tyr Asn
```

|  |  |  |  |  |  |  |  |  |  |  |  |  |  |  |  | |
|---|---|---|---|---|---|---|---|---|---|---|---|---|---|---|---|---|
| tcc | tcc | ctc | aag | agt | cgc | atc | acc | ctg | tca | cta | gac | gcg | tcc | aag | aac | 288 |
| Ser | Ser | Leu | Lys | Ser | Arg | Ile | Thr | Leu | Ser | Leu | Asp | Ala | Ser | Lys | Asn |  |
|  |  |  |  | 85 |  |  |  |  | 90 |  |  |  |  | 95 |  |  |
| cag | ttc | tcc | ctg | aac | ctg | agc | tct | gtg | acc | gcc | gcg | gac | acg | gcc | gtg | 336 |
| Gln | Phe | Ser | Leu | Asn | Leu | Ser | Ser | Val | Thr | Ala | Ala | Asp | Thr | Ala | Val |  |
|  |  |  | 100 |  |  |  |  | 105 |  |  |  |  | 110 |  |  |  |
| tac | tac | tgt | gcc | aga | gat | cgg | ggc | tac | ggt | gcc | agc | aat | gat | gct | ttt | 384 |
| Tyr | Tyr | Cys | Ala | Arg | Asp | Arg | Gly | Tyr | Gly | Ala | Ser | Asn | Asp | Ala | Phe |  |
|  |  |  | 115 |  |  |  |  | 120 |  |  |  |  | 125 |  |  |  |
| gat | ttc | tgg | ggc | caa | ggg | ctc | agg | gtc | acc | gtc | tct | tca |  |  |  | 423 |
| Asp | Phe | Trp | Gly | Gln | Gly | Leu | Arg | Val | Thr | Val | Ser | Ser |  |  |  |  |
|  |  |  | 130 |  |  |  |  | 135 |  |  |  | 140 |  |  |  |  |

<210> SEQ ID NO 41
<211> LENGTH: 411
<212> TYPE: DNA
<213> ORGANISM: Macaca cynomolgus
<220> FEATURE:
<221> NAME/KEY: CDS
<222> LOCATION: (1)...(411)

<400> SEQUENCE: 41

|  |  |  |  |  |  |  |  |  |  |  |  |  |  |  |  | |
|---|---|---|---|---|---|---|---|---|---|---|---|---|---|---|---|---|
| atg | aag | cac | ctg | tgg | ttc | ttc | ctc | ctc | ctg | gtg | gca | act | cct | aaa | tgg | 48 |
| Met | Lys | His | Leu | Trp | Phe | Phe | Leu | Leu | Leu | Val | Ala | Thr | Pro | Lys | Trp |  |
| 1 |  |  |  | 5 |  |  |  |  | 10 |  |  |  |  | 15 |  |  |
| gtc | ctg | tcc | cag | gtg | cag | ttg | cat | gag | tcg | ggc | cct | gga | ctg | ctg | aag | 96 |
| Val | Leu | Ser | Gln | Val | Gln | Leu | His | Glu | Ser | Gly | Pro | Gly | Leu | Leu | Lys |  |
|  |  |  | 20 |  |  |  |  | 25 |  |  |  |  | 30 |  |  |  |
| cct | tcg | gag | acc | ctg | tcc | ctc | acc | tgc | aat | gtc | tcc | ggt | gac | tcc | ccc | 144 |
| Pro | Ser | Glu | Thr | Leu | Ser | Leu | Thr | Cys | Asn | Val | Ser | Gly | Asp | Ser | Pro |  |
|  |  | 35 |  |  |  |  | 40 |  |  |  |  | 45 |  |  |  |  |
| act | aag | tcc | acg | tgg | aac | tgg | gtc | cgc | cag | tcc | cca | ggg | aag | cca | ctg | 192 |
| Thr | Lys | Ser | Thr | Trp | Asn | Trp | Val | Arg | Gln | Ser | Pro | Gly | Lys | Pro | Leu |  |
|  | 50 |  |  |  |  | 55 |  |  |  |  | 60 |  |  |  |  |  |
| gaa | tgg | att | ggt | cat | gtc | ggt | tct | ggt | gga | ggt | ggc | ccc | gtt | tac | aac | 240 |
| Glu | Trp | Ile | Gly | His | Val | Gly | Ser | Gly | Gly | Gly | Gly | Pro | Val | Tyr | Asn |  |
| 65 |  |  |  |  | 70 |  |  |  |  | 75 |  |  |  |  | 80 |  |
| gtc | ttc | ttg | acg | ggt | cgc | gtc | tcc | atg | tct | cta | gac | gct | tca | aag | aag | 288 |
| Val | Phe | Leu | Thr | Gly | Arg | Val | Ser | Met | Ser | Leu | Asp | Ala | Ser | Lys | Lys |  |
|  |  |  |  | 85 |  |  |  |  | 90 |  |  |  |  | 95 |  |  |
| ctt | ctc | tcc | ctg | gcc | tta | gca | tct | gtg | acc | gcc | gcc | gac | tcg | gcc | gtc | 336 |
| Leu | Leu | Ser | Leu | Ala | Leu | Ala | Ser | Val | Thr | Ala | Ala | Asp | Ser | Ala | Val |  |
|  |  |  | 100 |  |  |  |  | 105 |  |  |  |  | 110 |  |  |  |
| tat | tac | tgt | gtc | aga | tcg | acg | gca | tta | ttt | tcg | ttg | gat | gtc | tgg | ggc | 384 |
| Tyr | Tyr | Cys | Val | Arg | Ser | Thr | Ala | Leu | Phe | Ser | Leu | Asp | Val | Trp | Gly |  |
|  |  |  | 115 |  |  |  |  | 120 |  |  |  |  | 125 |  |  |  |
| cgg | gga | ctt | ctg | gtc | acc | gtc | tcc | tca |  |  |  |  |  |  |  | 411 |
| Arg | Gly | Leu | Leu | Val | Thr | Val | Ser | Ser |  |  |  |  |  |  |  |  |
|  | 130 |  |  |  |  | 135 |  |  |  |  |  |  |  |  |  |  |

<210> SEQ ID NO 42
<211> LENGTH: 442
<212> TYPE: DNA
<213> ORGANISM: Macaca cynomolgus
<220> FEATURE:
<221> NAME/KEY: CDS
<222> LOCATION: (1)...(441)

<400> SEQUENCE: 42

|  |  |  |  |  |  |  |  |  |  |  |  |  |  |  |  | |
|---|---|---|---|---|---|---|---|---|---|---|---|---|---|---|---|---|
| atg | gag | ttg | gga | ctg | agc | tgg | gtt | ttc | ctt | ctt | gtt | gct | att | tta | aaa | 48 |
| Met | Glu | Leu | Gly | Leu | Ser | Trp | Val | Phe | Leu | Leu | Val | Ala | Ile | Leu | Lys |  |
| 1 |  |  |  | 5 |  |  |  |  | 10 |  |  |  |  | 15 |  |  |

```
ggt gtc cag tgt gac aag cag ctg gtg cag tcg ggg gga ggc ttg gtc       96
Gly Val Gln Cys Asp Lys Gln Leu Val Gln Ser Gly Gly Gly Leu Val
            20                  25                  30 cag cct ggc ggg tct ctg aga ctc gcc tgt gta gcc tcc gga ttc ccc      144
Gln Pro Gly Gly Ser Leu Arg Leu Ala Cys Val Ala Ser Gly Phe Pro
        35                  40                  45 ttc agt gac tat tac atg agt tgg gtc cgc cag gct cca ggg aag ggg      192
Phe Ser Asp Tyr Tyr Met Ser Trp Val Arg Gln Ala Pro Gly Lys Gly
    50                  55                  60 ttg gag tgg ctt gga tta att aaa acc aat cct gat ggt gga acg aca      240
Leu Glu Trp Leu Gly Leu Ile Lys Thr Asn Pro Asp Gly Gly Thr Thr
65                  70                  75                  80 gat tac gcc gcg tct gtg aaa ggc aga ttt atc atc tca cga gat gat      288
Asp Tyr Ala Ala Ser Val Lys Gly Arg Phe Ile Ile Ser Arg Asp Asp
                85                  90                  95 tca aag aac tca ctg ttc ctt caa atg aac agc ctg aaa acc gag gac      336
Ser Lys Asn Ser Leu Phe Leu Gln Met Asn Ser Leu Lys Thr Glu Asp
            100                 105                 110 acg gcc gtg tat tac tgc acc aca gaa gtg ttg gtg gtg tct gct att      384
Thr Ala Val Tyr Tyr Cys Thr Thr Glu Val Leu Val Val Ser Ala Ile
        115                 120                 125 caa ctc att gga tgt ctg ggg ccc ggg gag ttg tgg tca ccc gtc tct      432
Gln Leu Ile Gly Cys Leu Gly Pro Gly Glu Leu Trp Ser Pro Val Ser
    130                 135                 140 ttc cgc ttc a                                                        442
Phe Arg Phe
145

<210> SEQ ID NO 43
<211> LENGTH: 407
<212> TYPE: DNA
<213> ORGANISM: Macaca cynomolgus
<220> FEATURE:
<221> NAME/KEY: CDS
<222> LOCATION: (1)...(405)

<400> SEQUENCE: 43 atg aag cac ctg tgg ttc ttc ctc ctc ctg gtg gca gct ccc aga tgg       48
Met Lys His Leu Trp Phe Phe Leu Leu Leu Val Ala Ala Pro Arg Trp
1               5                   10                  15 gtc ctg tcc cag gtg cag ttg gag gag tcg ggc cca gga ctg gtg aag       96
Val Leu Ser Gln Val Gln Leu Glu Glu Ser Gly Pro Gly Leu Val Lys
            20                  25                  30 ccc tcg gag acc ctg tcc ctc acc tgc gct gtg tct ggt ggc ctc att      144
Pro Ser Glu Thr Leu Ser Leu Thr Cys Ala Val Ser Gly Gly Leu Ile
        35                  40                  45 act gga aac tac tgg aac tgg ctc cgg cag tca gaa ggg aag gga ctg      192
Thr Gly Asn Tyr Trp Asn Trp Leu Arg Gln Ser Glu Gly Lys Gly Leu
    50                  55                  60 gag tgg att ggc cat att ggt ggt agt agt ggg aac acc ggc tac aac      240
Glu Trp Ile Gly His Ile Gly Gly Ser Ser Gly Asn Thr Gly Tyr Asn
65                  70                  75                  80 tcc gct ttc gag agt cgc gtc acc ttg tca aga gac acg gcc aag aat      288
Ser Ala Phe Glu Ser Arg Val Thr Leu Ser Arg Asp Thr Ala Lys Asn
                85                  90                  95 cgg ttc tcc ctg aaa ctg acc tct gtg acc gcc gca gat tcg gcc gtc      336
Arg Phe Ser Leu Lys Leu Thr Ser Val Thr Ala Ala Asp Ser Ala Val
            100                 105                 110 tat tac tgt gcg aga tcg ggt ttt acc ggc acc gac ttc ttt tac tat      384
Tyr Tyr Cys Ala Arg Ser Gly Phe Thr Gly Thr Asp Phe Phe Tyr Tyr
        115                 120                 125
```

```
tgg ggc ccg ggg aag tct tgg tc                                    407
Trp Gly Pro Gly Lys Ser Trp
    130                 135

<210> SEQ ID NO 44
<211> LENGTH: 420
<212> TYPE: DNA
<213> ORGANISM: Macaca cynomolgus
<220> FEATURE:
<221> NAME/KEY: CDS
<222> LOCATION: (1)...(420)

<400> SEQUENCE: 44 atg aag cac ctg tgg ttc ttc ctc ctc ctg gtg gca gct ccc aga tgg    48
Met Lys His Leu Trp Phe Phe Leu Leu Leu Val Ala Ala Pro Arg Trp
 1               5                  10                  15 gtc ctg tcc cag gtt caa cta cag gag tcg ggc cca gga ctg atg aag    96
Val Leu Ser Gln Val Gln Leu Gln Glu Ser Gly Pro Gly Leu Met Lys
            20                  25                  30 cct tcg gag acc ctg tcc ctc acc tgc gct gtc tct ggt ggc tcc atc   144
Pro Ser Glu Thr Leu Ser Leu Thr Cys Ala Val Ser Gly Gly Ser Ile
        35                  40                  45 agc ggt ggt ttt ggc tgg ggc tgg atc cgt cag tcc ccg ggg aag ggg   192
Ser Gly Gly Phe Gly Trp Gly Trp Ile Arg Gln Ser Pro Gly Lys Gly
    50                  55                  60 ctg gaa tgg att gga agt ttc tat act act act gga aat acc ttc tcc   240
Leu Glu Trp Ile Gly Ser Phe Tyr Thr Thr Thr Gly Asn Thr Phe Ser
 65                  70                  75                  80 aac ccc tcc ctc aag agt cga gtc acc att tca gcg gac acg tcc aag   288
Asn Pro Ser Leu Lys Ser Arg Val Thr Ile Ser Ala Asp Thr Ser Lys
                85                  90                  95 aac cag ttc tcc ctg aga ctg acc tct gtg acc gcc gcg gac acg gcc   336
Asn Gln Phe Ser Leu Arg Leu Thr Ser Val Thr Ala Ala Asp Thr Ala
            100                 105                 110 gtt tat tac tgt gcg aga gat ctc tat agc agc ggc tat aaa ttt tac   384
Val Tyr Tyr Cys Ala Arg Asp Leu Tyr Ser Ser Gly Tyr Lys Phe Tyr
        115                 120                 125 tac tgg ggc cag gga gtc ctg gtc acc gtc tcc tca                   420
Tyr Trp Gly Gln Gly Val Leu Val Thr Val Ser Ser
    130                 135                 140

<210> SEQ ID NO 45
<211> LENGTH: 98
<212> TYPE: PRT
<213> ORGANISM: Macaca cynomolgus
<220> FEATURE:
<221> NAME/KEY: DOMAIN
<222> LOCATION: (31)...(35)
<223> OTHER INFORMATION: CDRI
<221> NAME/KEY: DOMAIN
<222> LOCATION: (50)...(66)
<223> OTHER INFORMATION: CDRII

<400> SEQUENCE: 45

Glu Val Gln Leu Val Glu Ser Gly Gly Gly Leu Val Gln Pro Gly Gly
 1               5                  10                  15

Ser Leu Arg Leu Ala Cys Val Gly Ser Gly Phe Ala Phe Arg Asn Thr
            20                  25                  30

Arg Met His Trp Ile Arg Gln Thr Pro Gly Lys Arg Leu Glu Trp Val
        35                  40                  45

Ala Asp Ile Lys Phe Asp Gly Ser Asp Phe Tyr Tyr Val Asp Ser Val
    50                  55                  60
```

-continued

```
Lys Gly Arg Phe Thr Ile Ser Arg Asp Asn Ala Lys Asn Ser Leu Tyr
 65                  70                  75                  80

Leu Glu Met Asn Ser Leu Arg Pro Asp Asp Thr Ala Val Tyr Phe Cys
                 85                  90                  95

Val Arg

<210> SEQ ID NO 46
<211> LENGTH: 98
<212> TYPE: PRT
<213> ORGANISM: Macaca cynomolgus
<220> FEATURE:
<221> NAME/KEY: DOMAIN
<222> LOCATION: (31)...(35)
<223> OTHER INFORMATION: CDRI
<221> NAME/KEY: DOMAIN
<222> LOCATION: (50)...(66)
<223> OTHER INFORMATION: CDRII

<400> SEQUENCE: 46

Gln Val Gln Leu Gln Glu Ser Gly Pro Gly Leu Val Lys Pro Ser Glu
  1               5                  10                  15

Thr Leu Ser Leu Thr Cys Thr Val Ser Gly Asp Ser Ile Thr Thr Val
                 20                  25                  30

Phe Trp Ser Trp Leu Arg Gln Ser Pro Gly Ile Gly Leu Glu Trp Ile
             35                  40                  45

Gly Asn Phe Ala Gly Ser Thr Pro Glu Thr Asn Tyr Asn Pro Ser Leu
     50                  55                  60

Lys Asn Arg Ala Thr Ile Ser Lys Asp Thr Pro Thr Asn Gln Phe Phe
 65                  70                  75                  80

Leu Arg Leu Thr Ser Val Thr Ala Ala Asp Thr Ala Val Tyr Phe Cys
                 85                  90                  95

Ala Arg

<210> SEQ ID NO 47
<211> LENGTH: 98
<212> TYPE: PRT
<213> ORGANISM: Macaca cynomolgus
<220> FEATURE:
<221> NAME/KEY: DOMAIN
<222> LOCATION: (31)...(35)
<223> OTHER INFORMATION: CDRI
<221> NAME/KEY: DOMAIN
<222> LOCATION: (50)...(66)
<223> OTHER INFORMATION: CDRII

<400> SEQUENCE: 47

Glu Val His Leu Val Gln Ser Gly Ala Gln Val Lys Arg Pro Gly Glu
  1               5                  10                  15

Ser Leu Arg Ile Ser Cys Lys Thr Ser Gly Tyr Thr Phe Thr Asp Ser
                 20                  25                  30

Trp Ile Ser Trp Val Arg Gln Met Pro Gly Lys Gly Leu Glu Trp Met
             35                  40                  45

Gly Asn Ile Tyr Pro Gly Asp Ser Asp Ser Arg Tyr Asn Pro Ser Phe
     50                  55                  60

Gln Gly Arg Val Thr Ile Ser Val Asp Lys Ser Ile Ser Thr Thr Tyr
 65                  70                  75                  80

Leu Gln Trp Ser Ser Leu Lys Ala Ser Asp Thr Ala Thr Tyr Tyr Cys
                 85                  90                  95

Ala Lys
```

```
<210> SEQ ID NO 48
<211> LENGTH: 98
<212> TYPE: PRT
<213> ORGANISM: Macaca cynomolgus
<220> FEATURE:
<221> NAME/KEY: DOMAIN
<222> LOCATION: (31)...(35)
<223> OTHER INFORMATION: CDRI
<221> NAME/KEY: DOMAIN
<222> LOCATION: (50)...(66)
<223> OTHER INFORMATION: CDRII

<400> SEQUENCE: 48

Gln Val Gln Leu Gln Glu Ser Gly Pro Gly Val Val Lys Pro Ser Glu
 1               5                  10                  15
Thr Leu Ser Leu Thr Cys Thr Val Ser Gly Gly Ser Phe Ser Thr Tyr
                20                  25                  30
Tyr Trp Asn Trp Ile Arg Gln Pro Pro Gly Lys Gly Leu Glu Trp Ile
            35                  40                  45
Gly Tyr Ile Gly Gly Gly Gly Arg Pro Asn Tyr Asn Ser Ser Leu
        50                  55                  60
Lys Ser Arg Ile Thr Leu Ser Leu Asp Ala Ser Lys Asn Gln Phe Ser
65                  70                  75                  80
Leu Asn Leu Ser Ser Val Thr Ala Ala Asp Thr Ala Val Tyr Tyr Cys
                85                  90                  95
Ala Arg

<210> SEQ ID NO 49
<211> LENGTH: 98
<212> TYPE: PRT
<213> ORGANISM: Macaca cynomolgus
<220> FEATURE:
<221> NAME/KEY: DOMAIN
<222> LOCATION: (31)...(35)
<223> OTHER INFORMATION: CDRI
<221> NAME/KEY: DOMAIN
<222> LOCATION: (50)...(66)
<223> OTHER INFORMATION: CDRII

<400> SEQUENCE: 49

Gln Val Gln Leu His Glu Ser Gly Pro Gly Leu Leu Lys Pro Ser Glu
 1               5                  10                  15
Thr Leu Ser Leu Thr Cys Asn Val Ser Gly Asp Ser Pro Thr Lys Ser
                20                  25                  30
Thr Trp Asn Trp Val Arg Gln Ser Pro Gly Lys Pro Leu Glu Trp Ile
            35                  40                  45
Gly His Val Gly Ser Gly Gly Gly Pro Val Tyr Asn Val Phe Leu
        50                  55                  60
Thr Gly Arg Val Ser Met Ser Leu Asp Ala Ser Lys Lys Leu Leu Ser
65                  70                  75                  80
Leu Ala Leu Ala Ser Val Thr Ala Ala Asp Ser Ala Val Tyr Tyr Cys
                85                  90                  95
Val Arg

<210> SEQ ID NO 50
<211> LENGTH: 100
<212> TYPE: PRT
<213> ORGANISM: Macaca cynomolgus
<220> FEATURE:
<221> NAME/KEY: DOMAIN
<222> LOCATION: (31)...(35)
<223> OTHER INFORMATION: CDRI
<221> NAME/KEY: DOMAIN
```

```
<222> LOCATION: (50)...(68)
<223> OTHER INFORMATION: CDRII

<400> SEQUENCE: 50
```

Asp Lys Gln Leu Val Gln Ser Gly Gly Leu Val Gln Pro Gly Gly
 1               5                  10                  15

Ser Leu Arg Leu Ala Cys Val Ala Ser Gly Phe Pro Phe Ser Asp Tyr
            20                  25                  30

Tyr Met Ser Trp Val Arg Gln Ala Pro Gly Lys Gly Leu Glu Trp Leu
        35                  40                  45

Gly Leu Ile Lys Thr Asn Pro Asp Gly Gly Thr Thr Asp Tyr Ala Ala
    50                  55                  60

Ser Val Lys Gly Arg Phe Ile Ile Ser Arg Asp Asp Ser Lys Asn Ser
65                  70                  75                  80

Leu Phe Leu Gln Met Asn Ser Leu Lys Thr Glu Asp Thr Ala Val Tyr
                85                  90                  95

Tyr Cys Thr Thr
            100

```
<210> SEQ ID NO 51
<211> LENGTH: 98
<212> TYPE: PRT
<213> ORGANISM: Macaca cynomolgus
<220> FEATURE:
<221> NAME/KEY: DOMAIN
<222> LOCATION: (31)...(35)
<223> OTHER INFORMATION: CDRI
<221> NAME/KEY: DOMAIN
<222> LOCATION: (50)...(66)
<223> OTHER INFORMATION: CDRII

<400> SEQUENCE: 51
```

Gln Val Gln Leu Glu Glu Ser Gly Pro Gly Leu Val Lys Pro Ser Glu
 1               5                  10                  15

Thr Leu Ser Leu Thr Cys Ala Val Ser Gly Gly Leu Ile Thr Gly Asn
            20                  25                  30

Tyr Trp Asn Trp Leu Arg Gln Ser Glu Gly Lys Gly Leu Glu Trp Ile
        35                  40                  45

Gly His Ile Gly Gly Ser Ser Gly Asn Thr Gly Tyr Asn Ser Ala Phe
    50                  55                  60

Glu Ser Arg Val Thr Leu Ser Arg Asp Thr Ala Lys Asn Arg Phe Ser
65                  70                  75                  80

Leu Lys Leu Thr Ser Val Thr Ala Ala Asp Ser Ala Val Tyr Tyr Cys
                85                  90                  95

Ala Arg

```
<210> SEQ ID NO 52
<211> LENGTH: 99
<212> TYPE: PRT
<213> ORGANISM: Macaca cynomolgus
<220> FEATURE:
<221> NAME/KEY: DOMAIN
<222> LOCATION: (31)...(36)
<223> OTHER INFORMATION: CDRI
<221> NAME/KEY: DOMAIN
<222> LOCATION: (51)...(67)
<223> OTHER INFORMATION: CDRII

<400> SEQUENCE: 52
```

Gln Val Gln Leu Gln Glu Ser Gly Pro Gly Leu Met Lys Pro Ser Glu
 1               5                  10                  15

```
Thr Leu Ser Leu Thr Cys Ala Val Ser Gly Gly Ser Ile Ser Gly Gly
            20                  25                  30

Phe Gly Trp Gly Trp Ile Arg Gln Ser Pro Gly Lys Gly Leu Glu Trp
        35                  40                  45

Ile Gly Ser Phe Tyr Thr Thr Thr Gly Asn Thr Phe Ser Asn Pro Ser
    50                  55                  60

Leu Lys Ser Arg Val Thr Ile Ser Ala Asp Thr Ser Lys Asn Gln Phe
65                  70                  75                  80

Ser Leu Arg Leu Thr Ser Val Thr Ala Ala Asp Thr Ala Val Tyr Tyr
                85                  90                  95

Cys Ala Arg

<210> SEQ ID NO 53
<211> LENGTH: 390
<212> TYPE: DNA
<213> ORGANISM: Macaca cynomolgus
<220> FEATURE:
<221> NAME/KEY: CDS
<222> LOCATION: (1)...(390)

<400> SEQUENCE: 53 atg gac ata agg gtc ccc gtg cag ctc ctg ggg ctc ctg ttg ctc tgg    48
Met Asp Ile Arg Val Pro Val Gln Leu Leu Gly Leu Leu Leu Leu Trp
 1               5                  10                  15 ctc cga ggt gcc aga tgt gac atc cag atg acc cag tct cca tcc tcc    96
Leu Arg Gly Ala Arg Cys Asp Ile Gln Met Thr Gln Ser Pro Ser Ser
            20                  25                  30 ctg tct aca tct gta gga gac act gtc acc atc act tgc cgg gcg agt   144
Leu Ser Thr Ser Val Gly Asp Thr Val Thr Ile Thr Cys Arg Ala Ser
        35                  40                  45 caa ggc att gac acg gag tta gcc tgg tat cag cag aaa cca ggt aaa   192
Gln Gly Ile Asp Thr Glu Leu Ala Trp Tyr Gln Gln Lys Pro Gly Lys
    50                  55                  60 gcc ccc aca ctc ctg atc tct gat gcc tcc agg ttg cag acg ggg gtc   240
Ala Pro Thr Leu Leu Ile Ser Asp Ala Ser Arg Leu Gln Thr Gly Val
65                  70                  75                  80 tca tct cgg ttc agc ggc agt gga tct gga aca gat ttc act ctc acc   288
Ser Ser Arg Phe Ser Gly Ser Gly Ser Gly Thr Asp Phe Thr Leu Thr
                85                  90                  95 atc aac agc ctg cag cct gaa gat att gcg act tat tac tgt caa cag   336
Ile Asn Ser Leu Gln Pro Glu Asp Ile Ala Thr Tyr Tyr Cys Gln Gln
            100                 105                 110 gat aat agt ttt cca ctc act ttc ggc gga ggg acc aag gtg gag atc   384
Asp Asn Ser Phe Pro Leu Thr Phe Gly Gly Gly Thr Lys Val Glu Ile
        115                 120                 125 aaa cga                                                            390
Lys Arg
    130

<210> SEQ ID NO 54
<211> LENGTH: 384
<212> TYPE: DNA
<213> ORGANISM: Macaca cynomolgus
<220> FEATURE:
<221> NAME/KEY: CDS
<222> LOCATION: (1)...(384)

<400> SEQUENCE: 54 gtc ttc att tcc ctg ttg ctc tgg atc tct ggt gcc tgt ggg gac att    48
Val Phe Ile Ser Leu Leu Leu Trp Ile Ser Gly Ala Cys Gly Asp Ile
 1               5                  10                  15
```

| | |
|---|---|
| gtg atg acc cag tct cca gac tcc ctg gct gtg tct ctg gga gag agg<br>Val Met Thr Gln Ser Pro Asp Ser Leu Ala Val Ser Leu Gly Glu Arg<br>20                 25                 30 | 96 |
| gtc acc atc aat tgt aag tcc agc cag agt ctt tta tac agc tcc aac<br>Val Thr Ile Asn Cys Lys Ser Ser Gln Ser Leu Leu Tyr Ser Ser Asn<br>     35                 40                 45 | 144 |
| aat aag aac tac tta gcc tgg tac cag caa aaa cca gga cag gct cct<br>Asn Lys Asn Tyr Leu Ala Trp Tyr Gln Gln Lys Pro Gly Gln Ala Pro<br>50                 55                 60 | 192 |
| caa cta ctc att tac tgg gca tct acc cgg gaa tcc ggg gtc cct aat<br>Gln Leu Leu Ile Tyr Trp Ala Ser Thr Arg Glu Ser Gly Val Pro Asn<br>65                 70                 75                 80 | 240 |
| cga ttt agt ggc agc ggc tct ggg aca gat ttc act ctc acc atc agt<br>Arg Phe Ser Gly Ser Gly Ser Gly Thr Asp Phe Thr Leu Thr Ile Ser<br>               85                 90                 95 | 288 |
| ggc ctg cag gct gaa gat gtg gca gtg tat tac tgt caa cag tat tat<br>Gly Leu Gln Ala Glu Asp Val Ala Val Tyr Tyr Cys Gln Gln Tyr Tyr<br>100                105               110 | 336 |
| gat atg ccc gac agt ttt ggc cag ggg acc aaa gtg gac atc aaa cga<br>Asp Met Pro Asp Ser Phe Gly Gln Gly Thr Lys Val Asp Ile Lys Arg<br>115                120               125 | 384 |

<210> SEQ ID NO 55
<211> LENGTH: 399
<212> TYPE: DNA
<213> ORGANISM: Macaca cynomolgus
<220> FEATURE:
<221> NAME/KEY: CDS
<222> LOCATION: (1)...(399)

<400> SEQUENCE: 55

| | |
|---|---|
| atg agg ctc cct gct cag ctc ctg ggg ctg cta ttg ctc tgc gtc ccc<br>Met Arg Leu Pro Ala Gln Leu Leu Gly Leu Leu Leu Leu Cys Val Pro<br>1                 5                 10                 15 | 48 |
| gga tcc agt ggg gat gtt gtg atg act cag tct cca ctc tcc ctg ccc<br>Gly Ser Ser Gly Asp Val Val Met Thr Gln Ser Pro Leu Ser Leu Pro<br>20                 25                 30 | 96 |
| gtc atc cct gga cag cca gcc tcc atc tcc tgc agg tct agt caa agc<br>Val Ile Pro Gly Gln Pro Ala Ser Ile Ser Cys Arg Ser Ser Gln Ser<br>     35                 40                 45 | 144 |
| ctt gta cat agt gac ggg aaa acc tac ttg aat tgg tta caa cag aag<br>Leu Val His Ser Asp Gly Lys Thr Tyr Leu Asn Trp Leu Gln Gln Lys<br>50                 55                 60 | 192 |
| cca ggc caa cct cca aga ctc ctg att tat cag gtt tct aac cgg cac<br>Pro Gly Gln Pro Pro Arg Leu Leu Ile Tyr Gln Val Ser Asn Arg His<br>65                 70                 75                 80 | 240 |
| tct ggg gtc cca gac aga ttc agc ggc agt ggg gca ggg aca gac ttc<br>Ser Gly Val Pro Asp Arg Phe Ser Gly Ser Gly Ala Gly Thr Asp Phe<br>               85                 90                 95 | 288 |
| aca ctg aaa atc agc aga gtg gag act gag gat gtt ggg gtt tat tcc<br>Thr Leu Lys Ile Ser Arg Val Glu Thr Glu Asp Val Gly Val Tyr Ser<br>100                105               110 | 336 |
| tgc gtg caa ggt aca cac tgg ccg tgg acg ttc ggc caa ggg acc aag<br>Cys Val Gln Gly Thr His Trp Pro Trp Thr Phe Gly Gln Gly Thr Lys<br>115                120               125 | 384 |
| gtg gac atc aaa cga<br>Val Asp Ile Lys Arg<br>130 | 399 |

<210> SEQ ID NO 56
<211> LENGTH: 384
<212> TYPE: DNA

<213> ORGANISM: Macaca cynomolgus
<220> FEATURE:
<221> NAME/KEY: CDS
<222> LOCATION: (1)...(384)

<400> SEQUENCE: 56

| atg agg gtc ccc gct cag ctc ctg ggg ctc ctg ctg ctc tgg ctc cca | 48 |
| Met Arg Val Pro Ala Gln Leu Leu Gly Leu Leu Leu Leu Trp Leu Pro | |
| 1               5                   10                  15 | |

| ggt gcc ata tgt gac att cag atg tcc cag tct cca tcc tcc ctg tct | 96 |
| Gly Ala Ile Cys Asp Ile Gln Met Ser Gln Ser Pro Ser Ser Leu Ser | |
|             20                  25                  30 | |

| gct tct gtg gga gac aga gtc acc atc acc tgc cgg gca agt cag ggc | 144 |
| Ala Ser Val Gly Asp Arg Val Thr Ile Thr Cys Arg Ala Ser Gln Gly | |
|         35                  40                  45 | |

| ata act aat tat tta aac tgg tat cag cag aaa ccg ggg aaa gcc cct | 192 |
| Ile Thr Asn Tyr Leu Asn Trp Tyr Gln Gln Lys Pro Gly Lys Ala Pro | |
|     50                  55                  60 | |

| aac ctc ctg atc tat tat gca act cgt ttg gcg agc ggg gtc cca tca | 240 |
| Asn Leu Leu Ile Tyr Tyr Ala Thr Arg Leu Ala Ser Gly Val Pro Ser | |
| 65                  70                  75                  80 | |

| agg ttc agc ggc agt gga tct ggg tcg gag tac agt ctc gcc atc agc | 288 |
| Arg Phe Ser Gly Ser Gly Ser Gly Ser Glu Tyr Ser Leu Ala Ile Ser | |
|                 85                  90                  95 | |

| agc ctg cag cct gaa gat ttt gca acc tat ttc tgt caa cag ggt tat | 336 |
| Ser Leu Gln Pro Glu Asp Phe Ala Thr Tyr Phe Cys Gln Gln Gly Tyr | |
|             100                 105                 110 | |

| agg gcc ccc tac act ttt ggc cag ggg acc aca gtg gag atc aaa cga | 384 |
| Arg Ala Pro Tyr Thr Phe Gly Gln Gly Thr Thr Val Glu Ile Lys Arg | |
|         115                 120                 125 | |

<210> SEQ ID NO 57
<211> LENGTH: 390
<212> TYPE: DNA
<213> ORGANISM: Macaca cynomolgus
<220> FEATURE:
<221> NAME/KEY: CDS
<222> LOCATION: (1)...(390)

<400> SEQUENCE: 57

| atg gac atg agg gtc ccc gct cag ctc ctg ggg ctc ctg ctg ctc tgg | 48 |
| Met Asp Met Arg Val Pro Ala Gln Leu Leu Gly Leu Leu Leu Leu Trp | |
| 1               5                   10                  15 | |

| ctc cta ggt gcc aga tgt gac atc cag atg acc cag tct cct tct tcc | 96 |
| Leu Leu Gly Ala Arg Cys Asp Ile Gln Met Thr Gln Ser Pro Ser Ser | |
|             20                  25                  30 | |

| ttg tct gca tct gta gga gac aga gtc acc atc act tgc caa gcc agt | 144 |
| Leu Ser Ala Ser Val Gly Asp Arg Val Thr Ile Thr Cys Gln Ala Ser | |
|         35                  40                  45 | |

| cag ggt att agc aac tgg tta gcc tgg tat cag cag aaa ccg ggg aaa | 192 |
| Gln Gly Ile Ser Asn Trp Leu Ala Trp Tyr Gln Gln Lys Pro Gly Lys | |
|     50                  55                  60 | |

| gcc cct aag ctc ctg atc tat gct gca tcc act ttc caa agt ggg gtc | 240 |
| Ala Pro Lys Leu Leu Ile Tyr Ala Ala Ser Thr Phe Gln Ser Gly Val | |
| 65                  70                  75                  80 | |

| cca tca agg ttc agc ggc agt gga tct ggg aca gag ttc act ctc acc | 288 |
| Pro Ser Arg Phe Ser Gly Ser Gly Ser Gly Thr Glu Phe Thr Leu Thr | |
|                 85                  90                  95 | |

| atc agc agc ctg cag cct gaa gat ttt gca act tac tac tgt caa cag | 336 |
| Ile Ser Ser Leu Gln Pro Glu Asp Phe Ala Thr Tyr Tyr Cys Gln Gln | |
|             100                 105                 110 | |

| tat aat act tac cct ctc act ttc ggc gga ggg acc aag gtg gag atc | 384 |

```
Tyr Asn Thr Tyr Pro Leu Thr Phe Gly Gly Gly Thr Lys Val Glu Ile
        115                 120                 125 aaa cga                                                              390
Lys Arg
    130

<210> SEQ ID NO 58
<211> LENGTH: 390
<212> TYPE: DNA
<213> ORGANISM: Macaca cynomolgus
<220> FEATURE:
<221> NAME/KEY: CDS
<222> LOCATION: (1)...(390)

<400> SEQUENCE: 58 atg gac ttg agg gcc ccc gct cat ctc cta ggg ctc ctg ctg ctc tgg    48
Met Asp Leu Arg Ala Pro Ala His Leu Leu Gly Leu Leu Leu Leu Trp
 1               5                  10                  15 ctc cca ggt gcc aga ggt gac atc cag atg acc cag tct cca ccc tcc    96
Leu Pro Gly Ala Arg Gly Asp Ile Gln Met Thr Gln Ser Pro Pro Ser
             20                  25                  30 ctg tct gcg tct gtt ggg gac act gtc agt ctt act tgt cgg gca agt   144
Leu Ser Ala Ser Val Gly Asp Thr Val Ser Leu Thr Cys Arg Ala Ser
         35                  40                  45 cag cct att ggc agt aat tta aat tgg ttc cag caa aaa cct ggg agc   192
Gln Pro Ile Gly Ser Asn Leu Asn Trp Phe Gln Gln Lys Pro Gly Ser
     50                  55                  60 ccc ccc aga ctc ctg atc tac ctt gcg acc gcc ttg caa cgt ggg atc   240
Pro Pro Arg Leu Leu Ile Tyr Leu Ala Thr Ala Leu Gln Arg Gly Ile
 65                  70                  75                  80 ccg tca agg ttt agc gcc act gga tct caa acc aat ttc act ctc acg   288
Pro Ser Arg Phe Ser Ala Thr Gly Ser Gln Thr Asn Phe Thr Leu Thr
                 85                  90                  95 atc acc ggc ctg cag cct gag gat ttc gca act tac ctc tgt ctg caa   336
Ile Thr Gly Leu Gln Pro Glu Asp Phe Ala Thr Tyr Leu Cys Leu Gln
            100                 105                 110 cat act tct tac cca ttc act ttt ggc ccc ggg aca aag gtg gat atc   384
His Thr Ser Tyr Pro Phe Thr Phe Gly Pro Gly Thr Lys Val Asp Ile
        115                 120                 125 aag cga                                                            390
Lys Arg
    130

<210> SEQ ID NO 59
<211> LENGTH: 88
<212> TYPE: PRT
<213> ORGANISM: Macaca cynomolgus
<220> FEATURE:
<221> NAME/KEY: DOMAIN
<222> LOCATION: (24)...(34)
<223> OTHER INFORMATION: CDRI
<221> NAME/KEY: DOMAIN
<222> LOCATION: (50)...(56)
<223> OTHER INFORMATION: CDRII

<400> SEQUENCE: 59

Asp Ile Gln Met Thr Gln Ser Pro Ser Ser Leu Ser Thr Ser Val Gly
 1               5                  10                  15

Asp Thr Val Thr Ile Thr Cys Arg Ala Ser Gln Gly Ile Asp Thr Glu
             20                  25                  30

Leu Ala Trp Tyr Gln Gln Lys Pro Gly Lys Ala Pro Thr Leu Leu Ile
         35                  40                  45

Ser Asp Ala Ser Arg Leu Gln Thr Gly Val Ser Ser Arg Phe Ser Gly
```

```
                50                  55                  60
Ser Gly Ser Gly Thr Asp Phe Thr Leu Thr Ile Asn Ser Leu Gln Pro
 65                  70                  75                  80

Glu Asp Ile Ala Thr Tyr Tyr Cys
                 85

<210> SEQ ID NO 60
<211> LENGTH: 94
<212> TYPE: PRT
<213> ORGANISM: Macaca cynomolgus
<220> FEATURE:
<221> NAME/KEY: DOMAIN
<222> LOCATION: (24)...(40)
<223> OTHER INFORMATION: CDRI
<221> NAME/KEY: DOMAIN
<222> LOCATION: (56)...(62)
<223> OTHER INFORMATION: CDRII

<400> SEQUENCE: 60

Asp Ile Val Met Thr Gln Ser Pro Asp Ser Leu Ala Val Ser Leu Gly
 1               5                  10                  15

Glu Arg Val Thr Ile Asn Cys Lys Ser Ser Gln Ser Leu Leu Tyr Ser
                20                  25                  30

Ser Asn Asn Lys Asn Tyr Leu Ala Trp Tyr Gln Gln Lys Pro Gly Gln
            35                  40                  45

Ala Pro Gln Leu Leu Ile Tyr Trp Ala Ser Thr Arg Glu Ser Gly Val
        50                  55                  60

Pro Asn Arg Phe Ser Gly Ser Gly Ser Gly Thr Asp Phe Thr Leu Thr
 65                  70                  75                  80

Ile Ser Gly Leu Gln Ala Glu Asp Val Ala Val Tyr Tyr Cys
                85                  90

<210> SEQ ID NO 61
<211> LENGTH: 93
<212> TYPE: PRT
<213> ORGANISM: Macaca cynomolgus
<220> FEATURE:
<221> NAME/KEY: DOMAIN
<222> LOCATION: (24)...(39)
<223> OTHER INFORMATION: CDRI
<221> NAME/KEY: DOMAIN
<222> LOCATION: (54)...(61)
<223> OTHER INFORMATION: CDRII

<400> SEQUENCE: 61

Asp Val Val Met Thr Gln Ser Pro Leu Ser Leu Pro Val Ile Pro Gly
 1               5                  10                  15

Gln Pro Ala Ser Ile Ser Cys Arg Ser Ser Gln Ser Leu Val His Ser
                20                  25                  30

Asp Gly Lys Thr Tyr Leu Asn Trp Leu Gln Gln Lys Pro Gly Gln Pro
            35                  40                  45

Pro Arg Leu Leu Ile Tyr Gln Val Ser Asn Arg His Ser Gly Val Pro
        50                  55                  60

Asp Arg Phe Ser Gly Ser Gly Ala Gly Thr Asp Phe Thr Leu Lys Ile
 65                  70                  75                  80

Ser Arg Val Glu Thr Glu Asp Val Gly Val Tyr Ser Cys
                85                  90

<210> SEQ ID NO 62
<211> LENGTH: 88
<212> TYPE: PRT
<213> ORGANISM: Macaca cynomolgus
```

```
<220> FEATURE:
<221> NAME/KEY: DOMAIN
<222> LOCATION: (24)...(34)
<223> OTHER INFORMATION: CDRI
<221> NAME/KEY: DOMAIN
<222> LOCATION: (50)...(56)
<223> OTHER INFORMATION: CDRII

<400> SEQUENCE: 62

Asp Ile Gln Met Ser Gln Ser Pro Ser Ser Leu Ser Ala Ser Val Gly
 1               5                  10                  15

Asp Arg Val Thr Ile Thr Cys Arg Ala Ser Gln Gly Ile Thr Asn Tyr
            20                  25                  30

Leu Asn Trp Tyr Gln Gln Lys Pro Gly Lys Ala Pro Asn Leu Leu Ile
        35                  40                  45

Tyr Tyr Ala Thr Arg Leu Ala Ser Gly Val Pro Ser Arg Phe Ser Gly
    50                  55                  60

Ser Gly Ser Gly Ser Glu Tyr Ser Leu Ala Ile Ser Ser Leu Gln Pro
65                  70                  75                  80

Glu Asp Phe Ala Thr Tyr Phe Cys
                85

<210> SEQ ID NO 63
<211> LENGTH: 88
<212> TYPE: PRT
<213> ORGANISM: Macaca cynomolgus
<220> FEATURE:
<221> NAME/KEY: DOMAIN
<222> LOCATION: (24)...(34)
<223> OTHER INFORMATION: CDRI
<221> NAME/KEY: DOMAIN
<222> LOCATION: (50)...(56)
<223> OTHER INFORMATION: CDRII

<400> SEQUENCE: 63

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Ala Ala Ser Thr Phe Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys
                85

<210> SEQ ID NO 64
<211> LENGTH: 88
<212> TYPE: PRT
<213> ORGANISM: Macaca cynomolgus
<220> FEATURE:
<221> NAME/KEY: DOMAIN
<222> LOCATION: (24)...(34)
<223> OTHER INFORMATION: CDRI
<221> NAME/KEY: DOMAIN
<222> LOCATION: (50)...(56)
<223> OTHER INFORMATION: CDRII

<400> SEQUENCE: 64

Asp Ile Gln Met Thr Gln Ser Pro Pro Ser Leu Ser Ala Ser Val Gly
 1               5                  10                  15
```

```
Asp Thr Val Ser Leu Thr Cys Arg Ala Ser Gln Pro Ile Gly Ser Asn
            20                  25                  30

Leu Asn Trp Phe Gln Lys Pro Gly Ser Pro Arg Leu Leu Ile
        35                  40                  45

Tyr Leu Ala Thr Ala Leu Gln Arg Gly Ile Pro Ser Arg Phe Ser Ala
        50                  55                  60

Thr Gly Ser Gln Thr Asn Phe Thr Leu Thr Ile Thr Gly Leu Gln Pro
65                  70                  75                  80

Glu Asp Phe Ala Thr Tyr Leu Cys
                85

<210> SEQ ID NO 65
<211> LENGTH: 360
<212> TYPE: DNA
<213> ORGANISM: Rat
<220> FEATURE:
<221> NAME/KEY: CDS
<222> LOCATION: (1)...(360)

<400> SEQUENCE: 65 gac acg gtg ctg acc cag tct cct gct ttg gct gtg cct cca gga gag     48
Asp Thr Val Leu Thr Gln Ser Pro Ala Leu Ala Val Pro Pro Gly Glu
 1               5                  10                  15 agg gtt acc gtc tcc tgt agg gcc agt gaa agt gtc agt aca ttt ttg     96
Arg Val Thr Val Ser Cys Arg Ala Ser Glu Ser Val Ser Thr Phe Leu
            20                  25                  30 cac tgg tat caa cag aaa cca gga cat caa ccc aaa ctc ctc atc tat    144
His Trp Tyr Gln Gln Lys Pro Gly His Gln Pro Lys Leu Leu Ile Tyr
        35                  40                  45 cta gcc tca aaa cta gaa tct ggg gtc cct gcc agg ttc agt ggc ggt    192
Leu Ala Ser Lys Leu Glu Ser Gly Val Pro Ala Arg Phe Ser Gly Gly
    50                  55                  60 ggg tct ggg aca gac ttc acc ctc acc att gat cct gtg gag gct gat    240
Gly Ser Gly Thr Asp Phe Thr Leu Thr Ile Asp Pro Val Glu Ala Asp
65                  70                  75                  80 gac act gct acc tat tac tgt cag cag acc tgg aat gat cct cgg acg    288
Asp Thr Ala Thr Tyr Tyr Cys Gln Gln Thr Trp Asn Asp Pro Arg Thr
                85                  90                  95 ttc ggt gga ggc acc aag ctg gaa ttg aaa cgg gct gat gct gca cca    336
Phe Gly Gly Gly Thr Lys Leu Glu Leu Lys Arg Ala Asp Ala Ala Pro
            100                 105                 110 act gta tct atc ttc cca cca tcc                                    360
Thr Val Ser Ile Phe Pro Pro Ser
            115                 120

<210> SEQ ID NO 66
<211> LENGTH: 360
<212> TYPE: DNA
<213> ORGANISM: Rat
<220> FEATURE:
<221> NAME/KEY: CDS
<222> LOCATION: (1)...(360)

<400> SEQUENCE: 66 gag gtc cag ctg cag cag tct gga cct gag gtt ggg agg cct ggg tcc     48
Glu Val Gln Leu Gln Gln Ser Gly Pro Glu Val Gly Arg Pro Gly Ser
 1               5                  10                  15 tca gtc aag att tct tgc aag gct tct ggc tac acc ttt aca gat tac     96
Ser Val Lys Ile Ser Cys Lys Ala Ser Gly Tyr Thr Phe Thr Asp Tyr
            20                  25                  30 gtt ttg aat tgg gtg aag cag agt cct gga cag gga ctg gaa tgg ata    144
Val Leu Asn Trp Val Lys Gln Ser Pro Gly Gln Gly Leu Glu Trp Ile
```

```
                35                  40                  45
gga tgg att gat cct gac tat ggt act act gat tat gct gag aag ttc    192
Gly Trp Ile Asp Pro Asp Tyr Gly Thr Thr Asp Tyr Ala Glu Lys Phe
         50                  55                  60 aaa aag aag gcc aca ctg act gca gat aca tcc tcc agc aca gcc tac    240
Lys Lys Lys Ala Thr Leu Thr Ala Asp Thr Ser Ser Ser Thr Ala Tyr
 65                  70                  75                  80 atc cag ctt agc agc ctg aca tct gag gac aca gcc acc tat ttt tgt    288
Ile Gln Leu Ser Ser Leu Thr Ser Glu Asp Thr Ala Thr Tyr Phe Cys
                 85                  90                  95 gct aga tct agg aat tac gga gga tat att aat tac tgg ggc caa gga    336
Ala Arg Ser Arg Asn Tyr Gly Gly Tyr Ile Asn Tyr Trp Gly Gln Gly
                100                 105                 110 gtc atg gtc aca gtc tcc tca gct                                    360
Val Met Val Thr Val Ser Ser Ala
            115                 120

<210> SEQ ID NO 67
<211> LENGTH: 109
<212> TYPE: PRT
<213> ORGANISM: Pan troglodytes

<400> SEQUENCE: 67

Ala Val His Met Thr Gln Ser Pro Ser Ser Leu Ser Ala Ser Val Gly
  1               5                  10                  15

Asp Ser Val Thr Ile Thr Cys Arg Ala Ser Gln Thr Ile Asn Ile Tyr
                 20                  25                  30

Leu Asn Trp Tyr Gln Gln Lys Pro Gly Lys Ala Pro Lys Leu Leu Ile
             35                  40                  45

Phe Asp Ala Ser Ile Leu Gln Ser Gly Val Pro Ser Arg Phe Ser Gly
         50                  55                  60

Ser Gly Ser Gly Thr Asp Phe Ser Leu Thr Ile Arg Ser Leu Gln Pro
 65                  70                  75                  80

Glu Asp Phe Ala Thr Tyr Tyr Cys Gln Cys Gly Trp Gly Thr His Pro
                 85                  90                  95

Tyr Asn Phe Gly Gln Gly Thr Lys Leu Glu Ile Lys Arg
                100                 105

<210> SEQ ID NO 68
<211> LENGTH: 108
<212> TYPE: PRT
<213> ORGANISM: Artificial Sequence
<220> FEATURE:
<223> OTHER INFORMATION: rat/chimpanzee sequence

<400> SEQUENCE: 68

Asp Thr Val Leu Thr Gln Ser Pro Ser Ser Leu Ser Ala Ser Val Gly
  1               5                  10                  15

Asp Ser Val Thr Ile Thr Cys Arg Ala Ser Glu Ser Val Ser Thr Phe
                 20                  25                  30

Leu His Trp Tyr Gln Gln Lys Pro Gly Lys Ala Pro Lys Leu Leu Ile
             35                  40                  45

Tyr Leu Ala Ser Lys Leu Glu Ser Gly Val Pro Ala Arg Phe Ser Gly
         50                  55                  60

Ser Gly Ser Gly Thr Asp Phe Ser Leu Thr Ile Arg Ser Leu Gln Pro
 65                  70                  75                  80

Glu Asp Phe Ala Thr Tyr Tyr Cys Gln Gln Thr Trp Asn Asp Pro Arg
                 85                  90                  95
```

Thr Phe Gly Gln Gly Thr Lys Leu Glu Ile Lys Arg
            100                 105

<210> SEQ ID NO 69
<211> LENGTH: 128
<212> TYPE: PRT
<213> ORGANISM: Pan troglodytes

<400> SEQUENCE: 69

Glu Val Gln Leu Val Glu Ser Gly Gly Val Val Gln Pro Gly Gly
  1               5                  10                  15

Ser Leu Arg Leu Ser Cys Ala Ala Ser Gly Phe Thr Phe Asp Asp Phe
            20                  25                  30

Ala Met His Trp Val Arg Gln Ala Pro Gly Lys Gly Leu Glu Trp Ile
            35                  40                  45

Ser Leu Val Ser Trp Asp Ser Tyr Asn Ile Tyr His Ala Asp Ser Val
            50                  55                  60

Lys Gly Arg Phe Thr Ile Ser Arg Asp Asn Arg Asn Ser Leu Tyr
 65                  70                  75                  80

Leu Gln Met Asn Asp Leu Arg Pro Glu Asp Thr Ala Ile Tyr Phe Cys
            85                  90                  95

Ala Lys Ala Asp Thr Gly Gly Asp Phe Asp Tyr Val Ser Asp Ser Trp
            100                 105                 110

Arg Cys Ala Leu Asp Tyr Trp Gly Gln Gly Thr Leu Val Thr Val Ser
            115                 120                 125

<210> SEQ ID NO 70
<211> LENGTH: 118
<212> TYPE: PRT
<213> ORGANISM: Artificial Sequence
<220> FEATURE:
<223> OTHER INFORMATION: rat/chimpanzee sequence

<400> SEQUENCE: 70

Glu Val Gln Leu Val Glu Ser Gly Gly Val Val Gln Pro Gly Gly
  1               5                  10                  15

Ser Leu Arg Leu Ser Cys Ala Ala Ser Gly Tyr Thr Phe Thr Asp Tyr
            20                  25                  30

Val Leu Asn Trp Val Lys Gln Ala Pro Gly Lys Gly Leu Glu Trp Ile
            35                  40                  45

Gly Trp Ile Asp Pro Asp Tyr Gly Thr Thr Asp Tyr Ala Glu Lys Phe
  50                  55                  60

Lys Lys Lys Ala Thr Leu Ser Ala Asp Thr Ser Arg Asn Ser Ala Tyr
 65                  70                  75                  80

Leu Gln Met Asn Asp Leu Arg Pro Glu Asp Thr Ala Ile Tyr Phe Cys
            85                  90                  95

Ala Arg Ser Arg Asn Tyr Gly Tyr Ile Asn Tyr Trp Gly Gln Gly
            100                 105                 110

Thr Leu Val Thr Val Ser
            115

<210> SEQ ID NO 71
<211> LENGTH: 354
<212> TYPE: DNA
<213> ORGANISM: Murine
<220> FEATURE:
<221> NAME/KEY: CDS
<222> LOCATION: (1)...(354)

<400> SEQUENCE: 71

```
caa gtt cag ctt caa cag tct gga gct gag ctg atg aag cct ggg gcc      48
Gln Val Gln Leu Gln Gln Ser Gly Ala Glu Leu Met Lys Pro Gly Ala
 1               5                  10                  15 tca gtg aag ata tcc tgc aag gct act ggc tac aca ttc agt agc tac      96
Ser Val Lys Ile Ser Cys Lys Ala Thr Gly Tyr Thr Phe Ser Ser Tyr
             20                  25                  30 tgg ata gag tgg gta aag cag agg cct gga cat ggc ctt gag tgg att     144
Trp Ile Glu Trp Val Lys Gln Arg Pro Gly His Gly Leu Glu Trp Ile
         35                  40                  45 gga gag att tta cct aga agt ggt aat act aac tac aat gag aag ttc     192
Gly Glu Ile Leu Pro Arg Ser Gly Asn Thr Asn Tyr Asn Glu Lys Phe
     50                  55                  60 aag ggc aag gcc aca ttc act gca gaa aca tcc tcc aac aca gcc tac     240
Lys Gly Lys Ala Thr Phe Thr Ala Glu Thr Ser Ser Asn Thr Ala Tyr
 65                  70                  75                  80 atg caa ctc agc agc ctg aca cct gag gac tct gcc gtc tat tac tgt     288
Met Gln Leu Ser Ser Leu Thr Pro Glu Asp Ser Ala Val Tyr Tyr Cys
                 85                  90                  95 tca agt cgc ggc gtc agg ggc tct atg gac tac tgg ggt caa gga acc     336
Ser Ser Arg Gly Val Arg Gly Ser Met Asp Tyr Trp Gly Gln Gly Thr
            100                 105                 110 tca gtc acc gtc tcc tca                                             354
Ser Val Thr Val Ser Ser
        115

<210> SEQ ID NO 72
<211> LENGTH: 324
<212> TYPE: DNA
<213> ORGANISM: Murine
<220> FEATURE:
<221> NAME/KEY: CDS
<222> LOCATION: (1)...(324)

<400> SEQUENCE: 72 gat att cag atg acc cag act aca tcc tcc ctg tct gcc tct ctg gga      48
Asp Ile Gln Met Thr Gln Thr Thr Ser Ser Leu Ser Ala Ser Leu Gly
 1               5                  10                  15 gac aga gtc acc atc act tgc agg tca agt cag gac att agc aat ttt      96
Asp Arg Val Thr Ile Thr Cys Arg Ser Ser Gln Asp Ile Ser Asn Phe
             20                  25                  30 tta aac tgg tat cag cag aaa cca gat gga act gtt aaa ctc ctg atc     144
Leu Asn Trp Tyr Gln Gln Lys Pro Asp Gly Thr Val Lys Leu Leu Ile
         35                  40                  45 tac tac aca tca aca tta cac tca gga gtc cca tca agg ttc agt ggc     192
Tyr Tyr Thr Ser Thr Leu His Ser Gly Val Pro Ser Arg Phe Ser Gly
     50                  55                  60 agt ggg tct gga aca gat tat tct ctc acc att agc aac ctg gag caa     240
Ser Gly Ser Gly Thr Asp Tyr Ser Leu Thr Ile Ser Asn Leu Glu Gln
 65                  70                  75                  80 gaa gat att gcc act tac ttt tgc caa cag ggt aat acg ctt cct tgg     288
Glu Asp Ile Ala Thr Tyr Phe Cys Gln Gln Gly Asn Thr Leu Pro Trp
                 85                  90                  95 acg ttc ggt gga ggc acc aac ctg gaa atc aaa cgg                     324
Thr Phe Gly Gly Gly Thr Asn Leu Glu Ile Lys Arg
            100                 105

<210> SEQ ID NO 73
<211> LENGTH: 108
<212> TYPE: PRT
<213> ORGANISM: Artificial Sequence
<220> FEATURE:
<223> OTHER INFORMATION: murine/chimpanzee sequence
```

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asp Ile Ser Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys Arg
            100                 105

<210> SEQ ID NO 74
<211> LENGTH: 118
<212> TYPE: PRT
<213> ORGANISM: Artificial Sequence
<220> FEATURE:
<223> OTHER INFORMATION: murine/chimpanzee sequence

<400> SEQUENCE: 74

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Trp Ile Glu Trp Val Lys Gln Ala Pro Gly Gln Gly Leu Glu Trp Ile
        35                  40                  45

Gly Glu Ile Leu Pro Arg Ser Gly Asn Thr Asn Tyr Asn Glu Lys Phe
    50                  55                  60

Lys Gly Lys Ala Ser Phe Asn Ala Asp Thr Ser Thr Asn Ile Ala Tyr
65                  70                  75                  80

Met Glu Leu Thr Ser Leu Arg Ser Glu Asp Thr Ala Val Tyr Tyr Cys
                85                  90                  95

Ser Ser Arg Gly Val Arg Gly Ser Met Asp Tyr Trp Gly Gln Gly Thr
            100                 105                 110

Leu Val Thr Val Ser Ser
        115

<210> SEQ ID NO 75
<211> LENGTH: 360
<212> TYPE: DNA
<213> ORGANISM: Murine
<220> FEATURE:
<221> NAME/KEY: CDS
<222> LOCATION: (1)...(360)

<400> SEQUENCE: 75 caa gtt cag ctt caa cag cct ggg gct gag ctt gtg aag tct ggg gcc      48
Gln Val Gln Leu Gln Gln Pro Gly Ala Glu Leu Val Lys Ser Gly Ala
1               5                   10                  15 tca gtg aag ctg tcc tgc aag gct tct ggc agt acc ttc acc agc tac      96
Ser Val Lys Leu Ser Cys Lys Ala Ser Gly Ser Thr Phe Thr Ser Tyr
            20                  25                  30 tgg atg cac tgg gtg aag cag agg cct gga cga ggc ctt gag tgg att     144
Trp Met His Trp Val Lys Gln Arg Pro Gly Arg Gly Leu Glu Trp Ile

```
                35              40              45
gga agg att gat cca aat agt ggt ggt act aag gat aat gag aag ttc      192
Gly Arg Ile Asp Pro Asn Ser Gly Gly Thr Lys Asp Asn Glu Lys Phe
        50              55              60 aag agc aag gcc aca ctg act gta gac aaa ccc tcc agc aca gcc tac      240
Lys Ser Lys Ala Thr Leu Thr Val Asp Lys Pro Ser Ser Thr Ala Tyr
 65              70              75              80 atg cag ctc agc agc ctg aca tct gag gac tct gcg gtc tat tat tgt      288
Met Gln Leu Ser Ser Leu Thr Ser Glu Asp Ser Ala Val Tyr Tyr Cys
                85              90              95 gca aga gag acc tac tat gat tcc tcg ttt gct tac tgg ggc caa ggg      336
Ala Arg Glu Thr Tyr Tyr Asp Ser Ser Phe Ala Tyr Trp Gly Gln Gly
            100             105             110 act ctg gtc act gtc tct gca gcc                                      360
Thr Leu Val Thr Val Ser Ala Ala
            115             120

<210> SEQ ID NO 76
<211> LENGTH: 336
<212> TYPE: DNA
<213> ORGANISM: Murine
<220> FEATURE:
<221> NAME/KEY: CDS
<222> LOCATION: (1)...(336)

<400> SEQUENCE: 76 gat att gtt atg act cag tct caa aaa ttc atg tcc aca tca gta gga       48
Asp Ile Val Met Thr Gln Ser Gln Lys Phe Met Ser Thr Ser Val Gly
 1               5              10              15 gac agg gtc agc gtc acc tgc aag gcc agt cag aat gtg ggt act aat       96
Asp Arg Val Ser Val Thr Cys Lys Ala Ser Gln Asn Val Gly Thr Asn
            20              25              30 gta gcc tgg tat caa cag aaa cca ggg caa tct cct aaa gca ctg att      144
Val Ala Trp Tyr Gln Gln Lys Pro Gly Gln Ser Pro Lys Ala Leu Ile
        35              40              45 tac tcg gca tcc tac cgg tac agt gga gtc cct gat cgc ttc aca ggc      192
Tyr Ser Ala Ser Tyr Arg Tyr Ser Gly Val Pro Asp Arg Phe Thr Gly
 50              55              60 agt gga tct ggg aca gat ttc act ctc acc atc agc aat gtg cag tct      240
Ser Gly Ser Gly Thr Asp Phe Thr Leu Thr Ile Ser Asn Val Gln Ser
 65              70              75              80 gaa gac ttg gca gag tat ttc tgt cag caa tat aac agc tat cct ctc      288
Glu Asp Leu Ala Glu Tyr Phe Cys Gln Gln Tyr Asn Ser Tyr Pro Leu
                85              90              95 acg ttc ggt gct ggg acc aag ctg gag ctg aaa cgg gct gat gct gca      336
Thr Phe Gly Ala Gly Thr Lys Leu Glu Leu Lys Arg Ala Asp Ala Ala
            100             105             110

<210> SEQ ID NO 77
<211> LENGTH: 107
<212> TYPE: PRT
<213> ORGANISM: Artificial Sequence
<220> FEATURE:
<223> OTHER INFORMATION: murine/chimpanzee sequence

<400> SEQUENCE: 77

Asp Ile Val Met Thr Gln Ser Pro Ser Ser Leu Ser Ala Ser Val Gly
 1               5              10              15

Asp Arg Val Thr Ile Thr Cys Lys Ala Ser Gln Asn Val Gly Thr Asn
            20              25              30

Val Ala Trp Tyr Gln Gln Lys Pro Gly Lys Ala Pro Lys Ala Leu Ile
        35              40              45
```

```
Tyr Ser Ala Ser Tyr Arg Tyr Ser Gly Val Pro Asp Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 78
<211> LENGTH: 118
<212> TYPE: PRT
<213> ORGANISM: Artificial Sequence
<220> FEATURE:
<223> OTHER INFORMATION: murine/chimpanzee sequence

<400> SEQUENCE: 78

Gln Val Gln Leu Val Gln Ser Gly Ala Glu Val Lys Lys Pro Gly Ser
 1               5                  10                  15

Ser Val Lys Val Ser Cys Lys Ala Ser Gly Ser Thr Phe Thr Ser Tyr
                20                  25                  30

Trp Met His Trp Val Lys Gln Ala Pro Gly Gln Gly Leu Glu Trp Ile
            35                  40                  45

Gly Arg Ile Asp Pro Asn Ser Gly Gly Thr Lys Asp Asn Glu Lys Phe
        50                  55                  60

Lys Ser Lys Ala Thr Leu Asn Val Asp Lys Ser Thr Asn Ile Ala Tyr
65                  70                  75                  80

Met Glu Leu Thr Ser Leu Arg Ser Glu Asp Thr Ala Val Tyr Tyr Cys
                85                  90                  95

Ala Arg Glu Thr Tyr Tyr Asp Ser Ser Phe Ala Tyr Trp Gly Gln Gly
                100                 105                 110

Thr Met Val Thr Val Ser
        115

<210> SEQ ID NO 79
<211> LENGTH: 119
<212> TYPE: PRT
<213> ORGANISM: Artificial Sequence
<220> FEATURE:
<223> OTHER INFORMATION: murine/human sequence

<400> SEQUENCE: 79

Gln Val Gln Leu Val Gln Ser Gly Ala Glu Val Lys Lys Pro Gly Ala
 1               5                  10                  15

Ser Val Lys Val Ser Cys Lys Ala Ser Gly Ser Thr Phe Thr Ser Tyr
                20                  25                  30

Trp Met His Trp Val Lys Gln Ala Pro Gly Gln Gly Leu Glu Trp Ile
            35                  40                  45

Gly Arg Ile Asp Pro Asn Ser Gly Gly Thr Lys Asp Asn Glu Lys Phe
        50                  55                  60

Lys Ser Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Thr Tyr Tyr Asp Ser Ser Phe Ala Tyr Trp Gly Gln Gly
                100                 105                 110

Thr Met Val Thr Val Ser Ala
```

<210> SEQ ID NO 80
<211> LENGTH: 102
<212> TYPE: PRT
<213> ORGANISM: Artificial Sequence
<220> FEATURE:
<223> OTHER INFORMATION: murine/human sequence

<400> SEQUENCE: 80

```
Asp Ile Val Met Thr Gln Ser Pro Ser Ser Leu Ser Ala Ser Val Gly
 1               5                  10                  15
Asp Arg Val Thr Ile Thr Cys Lys Ala Ser Gln Asn Val Gly Thr Asn
                20                  25                  30
Val Ala Trp Tyr Gln Gln Lys Pro Gly Lys Ala Pro Lys Ala Leu Ile
            35                  40                  45
Tyr Ser Ala Ser Tyr Arg Tyr Ser Gly Val Pro Asp Arg Phe Ser Gly
50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ser Tyr Pro Leu
                85                  90                  95
Thr Phe Gly Gly Gly Thr
            100
```

<210> SEQ ID NO 81
<211> LENGTH: 11
<212> TYPE: PRT
<213> ORGANISM: Pan troglodytes

<400> SEQUENCE: 81

```
Trp Gly Gln Gly Thr Met Val Thr Val Ser Ser
 1               5                  10
```

<210> SEQ ID NO 82
<211> LENGTH: 11
<212> TYPE: PRT
<213> ORGANISM: Pan troglodytes

<400> SEQUENCE: 82

```
Trp Gly Gln Gly Thr Leu Val Thr Val Ser Ser
 1               5                  10
```

<210> SEQ ID NO 83
<211> LENGTH: 11
<212> TYPE: PRT
<213> ORGANISM: Pan troglodytes

<400> SEQUENCE: 83

```
Trp Gly Pro Gly Thr Leu Val Thr Val Ser Ser
 1               5                  10
```

<210> SEQ ID NO 84
<211> LENGTH: 11
<212> TYPE: PRT
<213> ORGANISM: Pan troglodytes

<400> SEQUENCE: 84

```
Trp Gly Gln Gly Ile Leu Val Thr Val Ser Ser
 1               5                  10
```

<210> SEQ ID NO 85

```
<211> LENGTH: 11
<212> TYPE: PRT
<213> ORGANISM: Pan troglodytes

<400> SEQUENCE: 85

Trp Gly Arg Gly Ile Leu Val Ile Val Ser Ser
 1               5                  10

<210> SEQ ID NO 86
<211> LENGTH: 11
<212> TYPE: PRT
<213> ORGANISM: Pan troglodytes

<400> SEQUENCE: 86

Phe Gly Gln Gly Thr Arg Leu Glu Ile Lys Arg
 1               5                  10

<210> SEQ ID NO 87
<211> LENGTH: 11
<212> TYPE: PRT
<213> ORGANISM: Pan troglodytes

<400> SEQUENCE: 87

Phe Gly Gln Gly Thr Lys Leu Glu Ile Lys Arg
 1               5                  10

<210> SEQ ID NO 88
<211> LENGTH: 11
<212> TYPE: PRT
<213> ORGANISM: Macaca cynomolgus

<400> SEQUENCE: 88

Trp Gly Arg Gly Val Leu Val Thr Val Ser Ser
 1               5                  10

<210> SEQ ID NO 89
<211> LENGTH: 11
<212> TYPE: PRT
<213> ORGANISM: Macaca cynomolgus

<400> SEQUENCE: 89

Trp Gly Gln Gly Val Gln Val Thr Val Ser Ser
 1               5                  10

<210> SEQ ID NO 90
<211> LENGTH: 11
<212> TYPE: PRT
<213> ORGANISM: Macaca cynomolgus

<400> SEQUENCE: 90

Trp Gly Pro Gly Val Met Val Thr Val Ser Ser
 1               5                  10

<210> SEQ ID NO 91
<211> LENGTH: 11
<212> TYPE: PRT
<213> ORGANISM: Macaca cynomolgus

<400> SEQUENCE: 91

Trp Gly Arg Gly Leu Leu Val Thr Val Ser Ser
 1               5                  10

<210> SEQ ID NO 92
<211> LENGTH: 11
<212> TYPE: PRT
```

```
<213> ORGANISM: Macaca cynomolgus

<400> SEQUENCE: 92

Trp Gly Gln Gly Val Leu Val Thr Val Ser Ser
  1               5                  10

<210> SEQ ID NO 93
<211> LENGTH: 11
<212> TYPE: PRT
<213> ORGANISM: Macaca cynomolgus

<400> SEQUENCE: 93

Trp Gly Gln Gly Leu Arg Val Thr Val Ser Ser
  1               5                  10

<210> SEQ ID NO 94
<211> LENGTH: 11
<212> TYPE: PRT
<213> ORGANISM: Macaca cynomolgus

<400> SEQUENCE: 94

Phe Gly Gln Gly Thr Lys Val Asp Ile Lys Arg
  1               5                  10

<210> SEQ ID NO 95
<211> LENGTH: 11
<212> TYPE: PRT
<213> ORGANISM: Macaca cynomolgus

<400> SEQUENCE: 95

Phe Gly Gln Gly Thr Thr Val Glu Ile Lys Arg
  1               5                  10

<210> SEQ ID NO 96
<211> LENGTH: 11
<212> TYPE: PRT
<213> ORGANISM: Macaca cynomolgus

<400> SEQUENCE: 96

Phe Gly Pro Gly Thr Lys Val Asp Ile Lys Arg
  1               5                  10

<210> SEQ ID NO 97
<211> LENGTH: 11
<212> TYPE: PRT
<213> ORGANISM: Pan troglodytes

<400> SEQUENCE: 97

Phe Gly Gly Gly Thr Lys Val Glu Ile Lys Arg
  1               5                  10
```

US 6,936,698 B2

MONOCLONAL ANTIBODIES WITH REDUCED IMMUNOGENICITY

This is a continuation of application Ser. No. 09/300,970 filed Apr. 28, 1999, now abandoned, which claims the benefit of U.S. Provisional Application No. 60/083,367, filed Apr. 28, 1998.

FIELD OF THE INVENTION

This invention relates to monoclonal antibodies (mAbs) having reduced immunogenicity in humans.

BACKGROUND OF THE INVENTION

Many potentially therapeutic mAbs are first generated in a murine hybridoma system for reasons of speed and simplicity. Non-human mAbs contain substantial stretches of amino acid sequences that will be immunogenic when injected into a human patient. It is well known that after injection of a foreign antibody, such as a murine antibody, a patient can have a strong human anti-mouse antibody (HAMA) response that essentially eliminates the antibody's therapeutic utility after the initial treatment as well as the utility of any other subsequently administered murine antibody.

Humanization techniques are well known for producing mAbs which exhibit reduced immunogenicity in humans while retaining the binding affinity of the original non-human parental mAb. See, e.g., those disclosed in U.S. Pat. Nos. 5,585,089; 5,693,761; 5,693,762; and 5,225,539.

In general, these methods depend on replacing human variable heavy and light region complementarity determining regions (CDRs) with antigen specific non-human CDRs, a process known as CDR grafting. It is also well known that in CDR grafting experiments the retention of the original antigen binding affinity is enhanced and in many cases depends on choosing human acceptor framework regions that most closely match the corresponding frameworks of the CDR donor antibody.

However, since the human genome contains a limited repertoire of heavy and light chain framework regions, these methods suffer from the limitation of available human acceptor frameworks. This restriction in acceptor framework repertoire necessarily can limit the degree of match between the non-human donor and the human acceptor antibody. Thus, CDR grafting methods are limited by the known available repertoire of human VH and VL framework regions. Clearly, a need exists for an expanded range of acceptor V regions.

SUMMARY OF THE INVENTION

One aspect of the present invention is an antibody comprising donor CDRs derived from an antigen-specific donor antibody of a non-human species and acceptor framework residues derived from a non-human primate.

Another aspect of the invention is a method for making an antibody having reduced immunogenicity in humans comprising grafting CDRs from antigen-specific non-human antibodies onto homologous non-human primate acceptor frameworks.

Another aspect of the invention is a chimpanzee VH acceptor framework I, II and III comprising an amino acid sequence as set forth in SEQ ID NOs: 10, 11, 12, 13, 14, 15, 16, 17 or 18.

Another aspect of the invention is a chimpanzee VH acceptor framework IV comprising an amino acid sequence as set forth in SEQ ID NOs: 81, 82, 83, 84 or 85.

Another aspect of the invention is a chimpanzee Vκ acceptor framework I, II and III comprising an amino acid sequence as set forth in SEQ ID NOs: 28, 29, 30, 31, 32, 33, 34, 35 or 36.

Another aspect of the invention is a chimpanzee Vκ acceptor framework IV comprising an amino acid sequence as set forth in SEQ ID NOs: 86 or 87.

Another aspect of the invention is a cynomolgus VH acceptor framework I, II and III comprising an amino acid sequence as set forth in SEQ ID NOs: 45, 46, 47, 48, 49, 50, 51 or 52.

Another aspect of the invention is a cynomolgus VH acceptor framework IV comprising an amino acid sequence as set forth in SEQ ID NOs: 88, 89, 90, 91, 92 or 93.

Another aspect of the invention is a cynomolgus Vκ acceptor framework I, II and III comprising an amino acid sequence as set forth in SEQ ID NOs: 59, 60, 61, 62, 63 or 64.

Another aspect of the invention is a cynomolgus Vκ acceptor framework IV comprising an amino acid sequence as set forth in SEQ ID NOs: 94, 95 or 96.

Yet another aspect of the invention is an isolated nucleic acid molecule encoding the amino acid sequence of SEQ ID NOs: 10, 11, 12, 13, 14, 15, 16, 17, 18, 28, 29, 30, 31, 32, 33, 34, 35 or 36.

Yet another aspect of the invention is an isolated nucleic acid molecule encoding the amino acid sequence of SEQ ID NOs: 81, 82, 83, 84, 85, 86 or 87.

Yet another aspect of the invention is an isolated nucleic acid molecule encoding the amino acid sequence of SEQ ID NOs: 45, 46, 47, 48, 49, 50, 51, 52, 59, 60, 61, 62, 63 or 64.

Yet another aspect of the invention is an isolated nucleic acid molecule encoding the amino acid sequence of SEQ ID NOs: 88, 89, 90, 91, 92, 93, 94, 95 or 96.

BRIEF DESCRIPTION OF THE DRAWINGS

FIG. 1 is an amino acid sequence of the engineered 4A6 VL region. Asterisks above the 4A6 sequence indicate the 4A6 framework residues retained in the engineered molecule. Bold and italicized letters indicate the CDRs.

FIG. 2 is an amino acid sequence of the engineered 4A6 VH region. Asterisks above the 4A6 sequence indicate the 4A6 framework residues retained in the engineered molecule. Bold and italicized letters indicate the CDRs.

FIG. 3 is an amino acid sequence alignment comparing the murine antibody B9Vκ with the closest matching chimpanzee Vκ and selected Jκ sequences. The CDR regions are indicated by bold and italicized letters. Gaps are indicated by dots. The numbering convention is from Kabat et al., infra.

FIG. 4 is an amino acid sequence alignment comparing the murine antibody B9VH with the closest matching chimpanzee VH and selected JH sequences. The CDR regions are indicated by bold and italicized letters. Gaps are indicated by dots. Asterisks indicate framework residues that are predicted to interact with CDRs and affect antigen binding affinity. The numbering convention is from Kabat et al., infra.

FIG. 5 is an amino acid sequence alignment comparing the murine antibody 3G9Vκ with the closest matching chimpanzee Vκ and selected Jk sequences. The CDR regions are indicated by bold and italicized letters. Gaps are indicated by dots. Asterisks indicate framework residues that are predicted to interact with CDRs and affect antigen binding affinity. The numbering convention is from Kabat et al., infra.

FIG. 6 is an amino acid sequence alignment comparing the murine antibody 3G9VH with the closest matching chimpanzee VH and selected JH sequences. The CDR regions are indicated by bold and italicized letters. Gaps are indicated by dots. Asterisks indicate framework residues that are predicted to interact with CDRs and affect antigen binding affinity. The numbering convention is from Kabat et al., infra.

DETAILED DESCRIPTION OF THE INVENTION

All publications, including but not limited to patents and patent applications, cited in this specification are herein incorporated by reference as though fully set forth.

The molecular genetic aspects of antibody structure have been reviewed by S. Tonegawa in *Nature* 302:575–581 (1983). Briefly, antibodies are heterodimers comprised of at least two heavy and two light chains. The N-terminal domain of each heavy and light chain, termed VH and VL, respectively, fold together to form the antigen combining site. On the genetic level, the VL domain is encoded by two different gene segments, termed Vκ or Vl, and Jκ or Jl that join together to form one continuous VL region. Similarly, the VH domain is encoded by three gene segments, VH, DH, and JH, that join together to form one continuous VH region. Thus different VL and VH regions may be encoded by different combinations of Vκ or Vl, Jκ or Jl and VH, DH, and JH. This combinatorial diversity is in part the means by which the immune response generates the myriad diversity of different antibody molecules and their associated antigen specificities.

On the protein level, each heavy and light V region domain may be further divided into three CDRs. Three heavy and three light chain CDRs fold together to form the antigen binding surface and part of the underlying support structures that are required to maintain the exact three-dimensional structure of the antigen combining site. Flanking each CDR are framework regions that in most cases do not directly interact with the specific antigen, but rather serve to form the scaffold which supports the antigen binding properties of the CDRs. Each heavy and light chain has four framework regions, three derived from the VH or VL gene segment, the fourth is derived from the JH, Jκ, or Jl gene segment. Thus, the order of frameworks and CDEs from the N-terminus is framework I, CDRI, framework II, CDRII, framework III, CDRIII, framework IV. On the genetic level, all of framework I through Framework III is encoded by the V region gene segment; CDRIII is encoded jointly by both the V region and J region gene segments; framework IV is encoded entirely from the J gene segment.

As used herein, "antibodies" refers to immunoglobulins and immunoglobulin fragments lacking all or part of an immunoglobulin constant region, e.g., Fv, Fab, Fab' or F(ab')$_2$ and the like.

The term "donor antibody" refers to a monoclonal or recombinant antibody which contributes the nucleic acid sequences of its variable regions, CDRs or other functional fragments or analogs thereof to an engineered antibody, so as to provide the engineered antibody coding region and resulting expressed engineered antibody with the antigenic specificity and neutralizing activity characteristic of the donor antibody.

The term "acceptor antibody" refers to monoclonal or recombinant antibodies heterologous to the donor antibody, which contributes all, or a portion, of the nucleic acid sequences encoding its heavy and/or light chain framework regions and/or its heavy and/or light chain constant regions or V region subfamily consensus sequences to the engineered antibody.

A "functional fragment" is a partial heavy or light chain variable sequence (e.g., minor deletions at the amino or carboxy terminus of the immunoglobulin variable region) which retains the same antigen binding specificity and affinity as the antibody from which the fragment was derived.

An "analog" is an amino acid sequence modified by at least one amino acid, wherein said modification can be chemical or a substitution, which modification permits the amino acid sequence to retain the biological characteristics, e.g., antigen specificity and high affinity, of the unmodified sequence.

Methods are provided for making engineered antibodies with reduced immunogenicity in humans and primates from non-human antibodies. CDRs from antigen-specific non-human antibodies, typically of rodent origin, are grafted onto homologous non-human primate acceptor frameworks. Preferably, the non-human primate acceptor frameworks are from Old World apes. Most preferably, the Old World ape acceptor framework is from *Pan troglodytes, Pan paniscus* or *Gorilla gorilla*. Particularly preferred is the chimpanzee *Pan troglodytes*. Also preferred are Old World monkey acceptor frameworks. Most preferably, the Old World monkey acceptor frameworks are from the genus *Macaca*. Particularly preferred is the *cynomolgus* monkey *Macaca cynomolgus*.

Particularly preferred chimpanzee (*Pan troglodytes*) heavy chain variable region frameworks (VH) are CPVH41-12 having the framework I, II and III amino acid sequence shown in SEQ ID NO: 10 and the framework IV amino acid sequence shown in SEQ ID NO: 83; CPVH41-1 having the framework I, II and III amino acid sequence shown in SEQ ID NO: 11 and the framework IV amino acid sequence shown in SEQ ID NO: 85; CPVH41-4 having the framework I, II and III amino acid sequence shown in SEQ ID NO: 12; CPVH41-7 having the framework I, II and III amino acid sequence shown in SEQ ID NO: 13; CPVH41-8 having the framework I, II and III amino acid sequence shown in SEQ ID NO: 14, CPVH41-9 having the framework I, II and III amino acid sequence shown in SEQ ID NO: 15 and the framework IV amino acid sequence shown in SEQ ID NO: 81; CPVH41-10 having the framework I, II and III amino acid sequence shown in SEQ ID NO: 16 and the framework IV amino acid sequence shown in SEQ ID NO: 82; CPVH41-18 having the framework I, II and III amino acid sequence shown in SEQ ID NO: 17; and CPVH41-19 having the framework I, II and III amino acid sequence shown in SEQ ID NO: 18 and the framework IV amino acid sequence shown in SEQ ID NO: 84.

Particularly preferred chimpanzee (*Pan troglodytes*) light chain kappa variable region frameworks (Vκ) are CPVκ46-1 having the framework I, II and III amino acid sequence shown in SEQ ID NO: 28; CPVκ46-3 having the framework I, II and III amino acid sequence shown in SEQ ID NO: 29; CPVκ46-4 having the framework I, II and III amino acid sequence shown in SEQ ID NO: 30; CPVκ46-5 having the framework I, II and III amino acid sequence shown in SEQ ID NO: 31; CPVκ46-6 having the framework I, II and III amino acid sequence shown in SEQ ID NO: 32 and the framework IV amino acid sequence shown in SEQ ID NO: 86; CPVκ46-7 having the framework I, II and III amino acid sequence shown in SEQ ID NO: 33 and the framework IV amino acid sequence shown in SEQ ID NO: 87; CPVκ46-8 having the framework I, II and III amino acid sequence shown in SEQ ID NO: 34; CPVκ46-11 having the framework I, II and III amino acid sequence shown in SEQ ID NO: 35; and CPVκ46-14 having the framework I, II and III amino acid sequence shown in SEQ ID NO: 36.

Particularly preferred *cynomolgus* (*Macaca cynomolgus*) heavy chain variable region frameworks (VH) are CYVH2-1 having the framework I, II and III amino acid sequence shown in SEQ ID NO: 45 and the framework IV amino acid sequence shown in SEQ ID NO: 88; CYVH2-3 having the framework I, II and III amino acid sequence shown in SEQ ID NO: 46 and the framework IV amino acid sequence shown in SEQ ID NO: 89; CYVH2-4 having the framework I, II and III amino acid sequence shown in SEQ ID NO: 47 and the framework IV amino acid sequence shown in SEQ ID NO: 90; CYVH2-5 having the framework I, II and III amino acid sequence shown in SEQ ID NO: 48 and the framework IV amino acid sequence shown in SEQ ID NO: 93; CYVH2-6 having the framework I, II and III amino acid sequence shown in SEQ ID NO: 49 and the framework IV amino acid sequence shown in SEQ ID NO: 91; CYVH2-7 having the framework I, II and III amino acid sequence shown in SEQ ID NO: 50; CYVH2-8 having the framework I, II and III amino acid sequence shown in SEQ ID NO: 51; and CYVH2-10 having the framework I, II and III amino acid sequence shown in SEQ ID NO: 52 and the framework IV amino acid sequence shown in SEQ ID NO: 92.

Particularly preferred *cynomolgus* (*Macaca cynomolgus*) light chain kappa variable region frameworks (Vκ) are CYVκ4-2 having the framework I, II and III amino acid sequence shown in SEQ ID NO: 59; CYVκ4-3 having the framework I, II and III amino acid sequence shown in SEQ ID NO: 60 and the framework IV amino acid sequence shown in SEQ ID NO: 94; CYVκ4-5 having the framework I, II and III amino acid sequence shown in SEQ ID NO: 61; CYVκ4-6 having the framework I, II and III amino acid sequence shown in SEQ ID NO: 62 and the framework IV amino acid sequence shown in SEQ ID NO: 95; CYVκ4-10 having the framework I, II and III amino acid sequence shown in SEQ ID NO: 63; and CYVκ4-11 having the framework I, II and III amino acid sequence shown in SEQ ID NO: 64 and the framework IV amino acid sequence shown in SEQ ID NO: 96.

Isolated nucleic acid molecules encoding the chimpanzee VH and Vκ acceptor framework I, II and III amino acid sequences of SEQ ID NOs: 10, 11, 12, 13, 14, 15, 16, 17, 18, 28, 29, 30, 31, 32, 33, 34, 35 or 36 and the framework IV amino acid sequences of SEQ ID NOs: 81, 82, 83, 84, 85, 86 or 87 are also part of the present invention. Further, isolated nucleic acid molecules encoding the *cynomolgus* VH and Vκ acceptor framework I, II and III amino acid sequences of SEQ ID NOs: 45, 46, 47, 48, 49, 50, 51, 52, 59, 60, 61, 62, 63 or 64 and the framework IV amino acid sequences of SEQ ID NOs: 88, 89, 90, 91, 92, 93, 94, 95 or 96 are also part of the present invention. Nucleic acid sequences encoding functional fragments or analogs of the VH and Vκ acceptor framework amino acid sequences are also part of the present invention.

In addition to isolated nucleic acid sequences encoding VH and Vk acceptor frameworks described herein, nucleic acid sequences complementary to these framework regions are also encompassed by the present invention. Useful DNA sequences include those sequences which hybridize under stringent hybridization conditions to the DNA sequences. See, T. Maniatis et al., *Molecular Cloning: A Laboratory Manual*, Cold Spring Harbor Laboratory (1982), pp. 387–389. An example of one such stringent hybridization condition is hybridization at 4×SSC at 65° C., followed by a washing in 0.1×SSC at 65° C. for one hour. Alternatively, an exemplary stringent hybridization condition is 50% formamide, 4×SSC at 42° C. Preferably, these hybridizing DNA sequences are at least about 18 nucleotides in length.

Suitable frameworks are selected by computer homology searching among members of a database of Old World ape or monkey VH and VL regions. The framework portions of primate antibodies are useful as components of therapeutic antibodies. Moreover, primate antibody frameworks will be tolerated when used in the treatment of humans due to the close sequence homology between the genes of the primates and humans. Thus, the present invention provides for the grafting of CDRs from an antigen specific non-human donor antibody to acceptor V regions derived from non-human primate species.

The antigen specificity and binding kinetics of the donor antibody, which may be of rodent or any other non-human origin, are best preserved by selecting primate acceptor V regions that are determined by computer homology searching to be most similar to the donor antibody. Alternatively, the acceptor antibody may be a consensus sequence generated from primate V region subfamilies, or portions thereof, displaying the highest homology to the donor antibody.

The resulting engineered constructs, in which the donor CDRs are grafted onto primate acceptor frameworks, are subsequently refined by analysis of three-dimensional models based on known antibody crystal structures as found, e.g., in the Protein Data Bank (PDB), which is operated by Rutgers, The State University of New Jersey; the San Diego Supercomputer Center at the University of California, San Diego; and the National Institute of Standards and Technology—three members of the Research Collaboratory for Structural Bioinformatics (RCSB) or a similar data bank containing three-dimensional protein structures. Alternatively, computer generated three-dimensional models of the donor antibody may be computed by means of commercially available software such as "AbM" (Oxford Molecular, Oxford, UK).

Structural analysis of these models may reveal donor framework residues that are CDR-contacting residues and that are seen to be important in the presentation of CDR loops, and therefore binding avidity. A CDR-contacting residue is one which is seen in three-dimensional models to come within the van der Waals radius of a CDR residue, or could interact with a CDR residue via a salt bridge or by hydrophobic interaction. Such donor framework (CDR-contacting) residues may be retained in the engineered construct.

The modeling experiments can also reveal which framework residues are largely exposed to the solvent environment. The engineered constructs may be further improved by substituting some or all of these solvent-accessible amino acid residues with those found at the same position among human V regions most homologous to the engineered construct as disclosed in U.S. Pat. No. 5,639,641.

The engineered V regions are then joined to one or more different human or Old World ape constant regions depending on the desired secondary immune functions such as complement fixation or Fc receptor binding. Human constant regions can be selected from human immunoglobulin classes and isotypes, such as IgG (subtypes 1 through 4), IgM, IgA, and IgE. An IgG4 subtype variant containing the mutations S228P and L235E (PE mutation) in the heavy chain constant region which results in reduced effector function can also be selected. See U.S. Pat. Nos. 5,624,821 and 5,648,260.

The complete heavy and light chain genes are transferred to suitable expression vectors and co-expressed in the appropriate host cells such as chinese hamster ovary, COS or myeloma cells. The resulting engineered antibody is expected to be of substantially reduced immunogenicity when administered to humans, and to retain full binding affinity for antigen.

Acceptor V regions can be isolated specifically for each donor V region by directed PCR methodology where a non-human primate cDNA library is surveyed for acceptor frameworks most similar to the donor antibody. Oligonucleotide PCR primers homologous to the donor antibody framework I (paired with C-region 3' PCR primers) are used to direct PCR amplification of a non-human primate, e.g., chimpanzee lymphocyte cDNA library. This would select for V-regions with framework I regions similar to the donor antibody, and sequence analysis of the obtained clones would reveal the associated framework II and III (and IV) sequences. 3' PCR primers would then be designed based on the knowledge of the non-human primate framework III sequences thus obtained, and used to direct PCR amplification of the original cDNA library together with a vector-specific 5' PCR primer. cDNA clones obtained from the second round of PCR amplification would have framework I and III sequences most similar to the donor antibody, and the framework II sequences would display a similar degree of sequence homology.

The present invention will now be described with reference to the following specific, non-limiting examples.

EXAMPLE 1

Random cDNA Cloning and Sequence Analysis of Chimpanzee VH Regions

Five ml of peripheral blood was collected and pooled from three chimpanzees (*Pan troglodytes*) and peripheral blood mononuclear cells were isolated by standard density centrifugation methods. These cells, which include antibody producing lymphocytes, were dissolved in TRIzol reagent (GIBCO, Gaithersburg, Md., USA) and total RNA was recovered from this material by solvent extraction and precipitation according to the manufacturer's specifications.

Chimpanzee heavy chain V regions were cloned from the total RNA using Marathon RACE methodology (Clontech, Palo Alto, Calif., USA) following exactly the manufacturer's protocol using 3' Cg1 gene specific primers. After RACE PCR amplification, DNA bands of the expected size were excised from agarose gels, the DNA was purified and cloned into a plasmid vector. Although this cDNA library contains many distinct heavy chain V region clones, nine were selected randomly for sequence analysis. Complete nucleic acid sequences and predicted protein sequences of the chimpanzee VH cDNA clones 41-12, 41-1, 41-4, 41-7, 41-8, 41-9, 41-10, 41-18 and 41-19 are shown in SEQ ID NOs: 1, 2, 3, 4, 5, 6, 7, 8 and 9, respectively. The amino acid sequences of the region from the first amino acid of the mature VH region to the second conserved cysteine residue at position 92, adjacent to CDR III of these clones, namely, CPVH41-12, CPVH41-1, CPVH41-4, CPVH41-7, CPVH41-8, CPVH41-9, CPVH41-10, CPVH41-18 and CPVH41-19 are shown in SEQ ID NOs: 10, 11, 12, 13, 14, 15, 16, 17 and 18, respectively. The amino acid sequence of the region encoding framework IV of these clones for CPVH41-9, CPVH41-10, CPVH41-12, CPVH41-19 and CPVH 41-1 are shown in SEQ ID NOs: 81, 82, 83, 84 and 85, respectively.

The chimpanzee VH amino acid sequences from the mature N-terminus and the second conserved cysteine residue at position 92, adjacent to CDRIII, were used as query sequences in computer homology searching of the Kabat database of Sequences of Proteins of Immunological Interest provided through the National Center for Biotechnology Information, which is operated by the National Library of Medicine and the National Institute of Health. The results of this analysis are shown in Table 1.

In each case, the closest match was with a human VH region, displaying between 76% (41-1/HHC20G) and 94% (41-10/HHC20Y) sequence identity at the amino acid level. Matches were found for each of the three major human VH subgroups, indicating that the chimpanzee VH repertoire includes at least some members homologous to each of the major human subgroups. The human subgroup homology is presented in Table 1.

TABLE 1

| Clone | Closest Match | Overall Amino Acid Homology | VH Subgroup Match |
|---|---|---|---|
| 41-4 | HHC10X | 88% | I |
| 41-9 | HHC10Y | 92 | I |
| 41-18 | HHC10D | 84 | I |
| 41-1 | HHC20G | 76 | II |
| 41-10 | HHC20Y | 94 | II |
| 41-12 | HHC20C | 83 | II |
| 41-7 | HHC30T | 80 | III |
| 41-8 | HHC30T | 79 | III |
| 41-19 | HHC305 | 82 | III |

The results show that the overall sequence identity between the chimpanzee and human VH regions ranged between 76 and 95% with a mean identity of 84%. Based on this observation, further sampling of the chimpanzee random VH library will likely provide a substantially greater diversity of VH sequences from which to choose optimum acceptor frameworks for each particular donor VH region.

EXAMPLE 2

Random cDNA Cloning and Sequence Analysis of Chimpanzee Vκ Regions

Chimpanzee light chain Vκ regions were cloned from the total RNA using Marathon RACE methodology (Clontech, Palo Alto, Calif., USA) following exactly the manufacturer's protocol and Cκ 3' gene specific primers. After RACE PCR amplification, DNA bands of the expected size were excised from agarose gels, the DNA was purified and cloned into a plasmid vector. Although this cDNA library contains many distinct light chain Vκ region clones, nine were selected randomly for sequence analysis. Complete nucleic acid sequences and predicted protein sequences of the chimpanzee Vκ cDNA clones 46-1, 46-3, 46-4, 46-5, 46-6, 46-7, 46-8, 46-11 and 46-14 are shown in SEQ ID NOs: 19, 20, 21, 22, 23, 24, 25, 26 and 27, respectively. The amino acid sequences of the region from the first amino acid of the mature Vκ region to the second conserved cysteine residue at position 88, adjacent to CDR III of these clones, namely CPVκ46-1, CPVκ46-3, CPVκ46-4, CPVκ46-5, CPVκ46-6, CPVκ46-7, CPVκ46-8, CPVκ46-11 and CPVκ46-14 are shown in SEQ ID NOs: 28, 29, 30, 31, 32, 33, 34, 35 and 36, respectively. The amino acid sequences of the region encoding framework IV of these clones for CPVκ46-6 and CPVκ46-7 are shown in SEQ ID NOs: 86 and 87, respectively.

The chimpanzee Vκ amino acid sequences comprising the mature N-terminus and the second conserved cysteine residue at position 88 were used as query sequences in computer homology searching of the Kabat database. The results of this analysis are shown in Table 2. In each case the closest match was with a human Vκ region, displaying between 68% (46-4/HKL310) and 97% (46-11/HKL106) sequence identity at the amino acid level. It is evident that the chimpanzee Vκ sequences are distinct from the collection of human Vκ found in the Kabat database.

The human subgroup homology is presented in Table 2. Of the four major human Vκ subgroups, matches were found for the two most frequently isolated, indicating that the chimpanzee Vκ repertoire is at least homologous to members of the majority of the human Vκ repertoire. Further sampling of the chimpanzee Vκ cDNA library will likely identify a greater diversity of chimpanzee Vκ regions, including ones homologous to the remaining two human Vκ subgroups (VκII and VκIV).

TABLE 2

| Clone | Closest Match | Overall Amino Acid Homology | VH Subgroup Match |
|---|---|---|---|
| 46-1 | HKL10C | 85% | I |
| 46-3 | HKL10O | 91 | I |
| 46-5 | HKL10O | 91 | I |
| 46-7 | HKL10O | 81 | I |
| 46-8 | HKL10N | 90 | I |
| 46-11 | HKL106 | 97 | I |
| 46-14 | HKL10O | 92 | I |
| 46-4 | HKL310 | 68 | III |
| 46-6 | HKL310 | 96 | III |

EXAMPLE 3

Random cDNA Cloning and Sequence Analysis of *Cynomolgus* VH Regions

Splenic RNA was recovered from a single donor *cynomolgus* monkey (*Macaca cynomolgus*) by means of standard laboratory practice. *Cynomolgus* heavy chain V regions were cloned from the total RNA using Marathon RACE methodology (Clontech, Palo Alto, Calif., USA) following exactly the manufacturer's protocol using 3' Cg1 gene specific primers. After RACE PCR amplification, DNA bands of the expected size were excised from agarose gels, the DNA was purified and cloned into a plasmid vector. Although this cDNA library contains many distinct heavy V region clones, eight were selected randomly for sequence analysis. Complete nucleic acid sequences and predicted protein sequences of the *Cynomolgus* VH cDNA clones 2-1, 2-3, 2-4, 2-5, 2-6, 2-7, 2-8 and 2-10 are shown in SEQ ID NOs: 37, 38, 39, 40, 41, 42, 43 and 44, respectively. The amino acid sequences of the region from the first amino acid of the mature VH region to the second conserved cysteine residue at position 92, adjacent to CDR III of these clones, namely CyVH2-1, CyVH2-3, CyVH2-4, CyVH2-5, CyVH2-6, CyVH2-7, CyVH2-8 and CyVH2-10 are shown in SEQ ID NOs: 45, 46, 47, 48, 49, 50, 51 and 52, respectively. The amino acid sequences of the region encoding framework IV of these clones for CyVH2-1, CyVH2-3, CyVH2-4, CyVH2-6, CyVH2-10 and CyVH2-5 are shown in SEQ ID NOs: 88, 89, 90, 91, 92 and 93, respectively.

The *cynomolgus* VH amino acid sequences from the mature N-terminus and the second conserved cysteine residue at position 92, adjacent to CDRIII, were used as query sequences in computer homology searching of the Kabat database. The results of this analysis are shown in Table 3. In each case the closest match was with a human VH region, displaying between 62% (2-6/HHC20E) and 84% (2-5/HHC20F) sequence identity at the amino acid level. It is evident that the *cynomolgus* VH sequences are distinct from the collection of human VH found in the Kabat database. Matches were found for each of the three major human VH subgroups, indicating that the *cynomolgus* VH repertoire includes at least some members homologous to each of the major human subgroups. The human subgroup homology is presented in Table 3.

TABLE 3

| Clone | Closest Match | Overall Amino Acid Homology | VH Subgroup Match |
|---|---|---|---|
| 2-4 | HHC10Y | 83% | I |
| 2-10 | HHC20G | 83 | II |
| 2-8 | HHC20F | 74 | II |
| 2-6 | HHC20E | 62 | II |
| 2-5 | HHC20F | 84 | II |
| 2-3 | HHC20F | 75 | II |
| 2-1 | HHC316 | 71 | III |
| 2-7 | HHC31C | 81 | III |

The results show that the overall sequence identity between the *cynomolgus* and human VH regions ranged between 62 and 84% with a mean identity of 77%. Based on this observation, further sampling of the *cynomolgus* random VH library will likely provide a substantially greater diversity of VH sequences from which to choose optimum acceptor frameworks for each particular donor VH region.

EXAMPLE 4

Random cDNA Cloning and Sequence Analysis of *Cynomolgus* Vκ Regions

*Cynomolgus* light chain Vκ regions were cloned from the total splenic RNA using Marathon RACE methodology (Clontech, Palo Alto, Calif., USA) following exactly the manufacturer's protocol and Cκ 3' gene specific primers. After RACE PCR amplification, DNA bands of the expected size were excised from agarose gels, the DNA was purified and cloned into a plasmid vector. Although this cDNA library contains many distinct light chain Vκ region clones, six were selected randomly for sequence analysis. Complete nucleic acid sequences and predicted protein sequences of the *Cynomolgus* Vκ cDNA clones 4-2, 4-3, 4-5, 4-6, 4-10 and 4-11 are shown in SEQ ID NOs: 53, 54, 55, 56, 57 and 58, respectively. The amino acid sequences of the region from the first amino acid of the mature Vκ region to the second conserved cysteine residue at position 88, adjacent to CDRIII, of these clones, namely CyVκ4-2, CyVκ4-3, CyVκ4-5, CyVκ4-6, CyVκ4-10 and CyVκ4-11 are shown in SEQ ID NOs: 59, 60, 61, 62, 63 and 64, respectively. The amino acid sequences encoding the framework IV region of these clones for CyVκ4-3, CyVκ4-6 and CyVκ4-11 are shown in SEQ ID NOs: 94, 95 and 96, respectively.

The *cynomolgus* Vκ amino acid sequences comprising the mature N-terminus and the second conserved cysteine residue at position 88 were used as query sequences in computer homology searching of the Kabat database. The results of this analysis are shown in Table 4. In each case the closest match was with a human Vκ region, displaying between 73% (4-11/HKL10S) and 94% (4-3/HKL400) sequence identity at the amino acid level. It is evident that the *cynomolgus* Vκ sequences are distinct from the collection of human Vκ found in the public genetic databases. The human subgroup homology is presented in Table 4. Matches were found for three of the four major human Vκ subgroups, indicating that the *cynomolgus* Vκ repertoire is largely homologous to members of the majority of the human Vκ repertoire. Further sampling of the *cynomolgus* Vκ cDNA library will likely identify a greater diversity of *cynomolgus* Vκ regions, including ones homologous to the remaining human Vκ subgroup (VκIII).

TABLE 4

| Clone | Closest Match | Overall Amino Acid Homology | VH Subgroup Match |
|---|---|---|---|
| 4-6 | HKL10L | 80% | I |
| 4-2 | HKL10Z | 83 | I |
| 4-11 | HKL10S | 73 | I |
| 4-10 | HKL10F | 93 | I |
| 4-5 | HKL209 | 86 | II |
| 4-3 | HKL400 | 94 | IV |

The results show that the overall sequence identity between the *cynomolgus* and human Vκ regions ranged between 73 and 94% with a mean identity of 85%. Based on this observation, further sampling of the *cynomolgus* random Vκ library will provide a substantially greater diversity of Vκ sequences from which to choose optimum acceptor frameworks for each particular donor Vκ region.

EXAMPLE 5

Preparation of Engineered Anti-IL-5 Monoclonal Antibodies

The Vκ and VH genes of the rat anti-interleukin-5 (IL-5) antibody 4A6 are shown in SEQ ID NOs: 65 and 66, respectively. These genes encode a high affinity neutralizing monoclonal antibody specific for human IL-5 useful for the treatment of asthma. See U.S. Pat. No. 5,693,323.

The 4A6 light chain was engineered as follows. The sequence of donor antibody Vκ4A6 (SEQ ID NO: 65) was aligned with the acceptor antibody light chain Vκ region from the chimpanzee Mab C108G (*Mol. Immunol.* 32:1081–1092 (1995)) (SEQ ID NO: 67) as shown in FIG. 1. Since native Vκ4A6 has a unique deletion of residue 10, the sequence alignment included the insertion of a gap at that position. The CDR residues were identified as defined by the convention of Kabat et al. in *Sequences of Proteins of Immunological Interest*, 4th ed., U.S. Department of Health and Human Services, National Institutes of Health (1987).

Framework residues that could influence CDR presentation were identified by analysis of three-dimensional models based on known antibody crystal structures. The residues of this CDR-contacting set were compared among the aligned Vκ4A6 and VκC108G sequences, and the positions of the set that differed between the Vκ4A6 and the VκC108G were marked (FIG. 1, asterisks). The CDRs and the marked framework residues of Vκ4A6 (the donor antibody) were transferred replacing the corresponding residues of VκC108G (the acceptor antibody). The completed engineered 4A6 light chain V region is shown in SEQ ID NO: 68. Six donor framework residues were retained in the engineered molecule at residues 1 to 4, 49 and 60.

In analogous fashion, a similar method was used to engineer the 4A6 heavy chain. The sequence of donor antibody VH4A6 (SEQ ID NO: 66) was aligned with the acceptor antibody heavy chain V region from the chimpanzee Mab C108G (SEQ ID NO: 69) as shown in FIG. 2. A large gap was introduced in the VH4A6 CDRIII alignment, as CDRIII of VHC108G is 10 residues longer. CDR residues were identified as defined by the convention of Kabat et al., supra.

Framework residues that could influence CDR presentation were identified by analysis of three-dimensional models based on known antibody crystal structures. The residues of this CDR-contacting set were compared among the aligned VH4A6 and VHC108G sequences, and the positions of the set that differed between the VH4A6 and the VHC108G were marked (FIG. 2, asterisks). In total, 11 such CDR contacting residues that differed between VH4A6 and the VHC108G were selected and marked. The CDRs and the marked CDR contacting framework residues of VH4A6 (the donor antibody) were transferred replacing the corresponding residues of VHC108G (the acceptor antibody). The completed engineered 4A6 heavy chain V region is shown in SEQ ID NO: 70. Eleven donor framework residues were retained in the engineered molecule at residues 27, 30, 38, 49, 66, 67, 69, 71, 73, 78 and 94.

The engineered 4A6 can be expressed in cells using methods well known to those skilled in the art. Briefly, genes encoding the complete engineered 4A6 VH and Vκ regions can be assembled from long synthetic oligonucleotides and ligated into appropriate eukaryotic expression vectors containing the desired antibody constant regions. Such an expression vector will contain selectable markers, for example, neomycin resistance and regulatory sequences, for example, the CMV promoter, required to direct the expression of full-length antibody heavy and light chains. Subsequently, transfection of the appropriate host cell, for example, chinese hamster ovary, would result in the expression of fully active engineered 4A6.

EXAMPLE 6

Preparation of Engineered Anti-Integrin Monoclonal Antibodies

The Vκ and VH genes of the murine anti-integrin antibody B9 are shown in SEQ ID NOs: 71 and 72, respectively. These genes encode a high affinity neutralizing monoclonal antibody specific for human integrin αvβ3 useful for the treatment of vascular diseases.

The B9 light chain was engineered as follows. The amino acid sequence of donor antibody VκB9 (SEQ ID NO: 72) was compared to each of the nine chimpanzee Vκ sequences described above and percent sequence identity determined by computer homology searching using the LASERGENE program "MEGALIGN" (DNASTAR, Inc., Madison, Wis.). Clones CPVκ46-3 (SEQ ID NO: 29) and CPVκ46-14 (SEQ ID NO: 36) were identified as the chimpanzee Vκ regions with the highest overall sequence similarity (77%) to the B9 donor Vκ. CPVκ46-3 was selected as the acceptor framework.

Similarly, the chimpanzee Jκ gene segment of CPVκ46-1 (SEQ ID NO: 97) was selected as acceptor framework IV. The sequences of the donor VκB9 and acceptor CPVκ46-3, CPVκ46-1 V regions were aligned and the positions of their respective framework and CDRs were determined as shown in FIG. 3.

The CDR residues were identified as defined by the convention of Kabat et al., supra. The results show that VκB9 and CPVκ46-3 share 77% overall sequence identity, with the framework regions I through III sharing 81% sequence identity.

Framework residues that could influence CDR presentation were identified by analysis of three-dimensional models based on known antibody crystal structures. The residues of this CDR-contacting set were compared among the aligned VκB9 and CPVκ46-3 sequences, and none of this set were found that differed between the VκB9 and the CPVκ46-3. Accordingly, only the CDRs of VκB9 (the donor antibody) were transferred replacing the corresponding residues of CPVκ46-3 (the acceptor antibody). Lastly, the framework IV sequences of CPVκ46-1 replaced the corresponding framework IV residues of the B9 light chain variable region. The completed engineered B9 light chain V region is shown in SEQ ID NO: 73. No donor framework residues were retained in the engineered light chain variable region.

The B9 heavy chain was engineered in analogous fashion. The amino acid sequence of donor antibody VHB9 (SEQ ID NO: 71) was compared to each of the nine chimpanzee VH sequences described above by computer homology searching. Clone CPVH41-18 (SEQ ID NO: 17) was identified as the chimpanzee VH region with the highest overall sequence similarity (58%) to the B9 donor VH.

The chimpanzee JH gene segment of CPVH41-10 (SEQ ID NO: 82) was selected as acceptor framework IV. The sequences of the donor VHB9 and chimpanzee acceptor V regions were aligned and the positions of their respective framework and CDRs determined as shown in FIG. 4.

The CDR residues were identified as defined by the convention of Kabat et al., supra. The results show that VHB9 and CPVH41-18 share 58% overall sequence identity, with the framework regions I through III sharing 65% sequence identity.

Framework residues that could influence CDR presentation were identified by analysis of three-dimensional models based on known antibody crystal structures. The residues of this CDR-contacting set were compared among the aligned VHB9 and CPVH41-18 sequences, and the nine residues of the set that differed between VHB9 and the chimpanzee acceptor frameworks were marked. The CDRs and the marked framework residues of donor antibody VHB9 were transferred replacing the corresponding residues of CPVH41-18 (the acceptor antibody). Lastly, the framework IV sequences of CPVH41-10 replaced the corresponding framework IV residues of the B9 heavy chain variable region. The completed engineered B9 heavy chain V region is shown in SEQ ID NO: 74. Nine donor framework residues were retained in the engineered heavy chain variable region at positions 24, 27, 38, 48, 66, 67, 69, 93 and 94.

EXAMPLE 7

Expression and Characterization of Engineered Anti-Integrin Monoclonal Antibodies The engineered B9 antibody was expressed in cells using methods well known to those skilled in the art. Briefly, genes encoding the complete engineered B9 VH and Vκ regions were assembled from long synthetic oligonucleotides and ligated into appropriate eukaryotic expression vectors containing IgG1,κ antibody constant regions. The expression vector contained a selectable marker for neomycin resistance and CMV promoter regulatory sequences. Subsequent transfection of a COS host cell resulted in the expression of engineered B9 (CPB9).

The relative binding avidity of CPB9 was compared to that of the original murine B9 antibody as follows. CPB9 antibodies present in culture supernatants from cells maintained in culture for 5 days after transfection with the expression constructs were compared to the parental murine B9 antibody using the ORIGEN technology (IGEN Inc, Gaithersburg, Md.). Briefly, different dilutions of the B9 variants were incubated with purified human αvβ3 integrin which had previously been biotinylated, and an electro-chemiluminescent TAG moiety specific for the antibody C regions. B9 variant antibody bound to the integrin was measured by capturing the immune complexes onto streptavidin beads followed by analysis on the ORIGEN instrument. The results showed that the CPB9 and the murine B9 binding curves were displaced only by about 3-fold indicating that the overall specific binding avidity of CPB9 and murine B9 for αvβ3 are within three-fold of each other. Accordingly, the results show that the CDR grafting of rodent CDRs onto chimpanzee frameworks as described in the present invention retained nearly all of the binding avidity of the parent rodent mAb.

EXAMPLE 8

Preparation of Engineered Anti-Erythropoietin Receptor Monoclonal Antibodies

The VH and Vκ genes of the murine anti-erythropoietin receptor antibody 3G9 are shown in SEQ ID NOs: 75 and 76, respectively. These genes encode a high affinity neutralizing monoclonal antibody specific for human erythropoietin receptor (EPOr) useful for the treatment of hematopoietic disorders.

The 3G9 light chain was engineered as follows. The amino acid sequence of donor antibody Vκ3G9 (SEQ ID NO: 76) was compared to each of the nine chimpanzee Vκ sequences described above by computer homology searching as described above. Clones CPVκ46-3 (SEQ ID NO: 29), CPVκ46-5 (SEQ ID NO: 31), CPVκ46-8 (SEQ ID NO: 34) and CPVκ46-14 (SEQ ID NO: 36) were identified as the chimpanzee Vκ regions with the highest overall sequence similarity (65%) to the 3G9 donor Vκ. CPVκ46-14 was selected as the acceptor framework.

The chimpanzee Jκ gene segment of CPVκ46-14 was identical to that of CPVκ46-1 (SEQ ID NO: 97) and was selected as acceptor framework IV. The sequences of the donor Vκ3G9 and acceptor CPVκ46-14 V regions were aligned and the positions of their respective framework and CDRs were determined as shown in FIG. 5.

The CDR residues were identified as defined by the convention of Kabat et al., supra. The results show that Vκ3G9 and CPVκ46-14 share 65% overall sequence identity, with the framework regions I through III sharing 73% sequence identity.

Framework residues that could influence CDR presentation were identified by analysis of three-dimensional models based on known antibody crystal structures. The residues of this CDR-contacting set were compared among the aligned Vκ3G9 and CPVκ46-14 sequences, and the positions of this set that differed between Vκ3G9 and the CPVκ46-3 were marked. The CDRs and marked residues of Vκ3G9 (the donor antibody) were transferred replacing the corresponding residues of CPVκ46-14 (the acceptor antibody). Lastly, the framework IV sequences of CPVκ46-14 replaced the corresponding framework IV residues of the 3G9 light chain variable region. The completed engineered 3G9 light chain V region is shown in SEQ ID NO: 77. Three donor framework residues were retained in the engineered light chain variable region at positions 3, 46 and 60.

The 3G9 heavy chain was engineered in analogous fashion. The amino acid sequence of donor antibody VH3G9 (SEQ ID NO: 75) was compared to each of the 9 chimpanzee VH sequences described above by computer homology searching. Clone CPVH41-18 (SEQ ID NO: 17) was identified as the chimpanzee VH region with the highest overall sequence similarity (53%) to the 3G9 donor VH.

The chimpanzee JH gene segment of CPVH41-18 was identical to CPVH41-9 (SEQ ID NO: 81) and was selected as acceptor framework IV. The sequences of the donor VH3G9 and chimpanzee acceptor V regions were aligned and the positions of their respective framework and CDRs determined as shown in FIG. 6.

The CDR residues were identified as defined by the convention of Kabat et al., supra. The results show that VH3G9 and CPVH41-18 share 53% overall sequence identity, with the framework regions I through III sharing 62% sequence identity.

Framework residues that could influence CDR presentation were identified by analysis of three-dimensional models based on known antibody crystal structures. The residues of this CDR-contacting set were compared among the aligned VH3G9 and CPVH41-18 sequences, and the twelve residues of the set that differed between VH3G9 and the chimpanzee acceptor frameworks were marked. The CDRs and the marked framework residues of donor antibody VH3G9 were transferred replacing the corresponding residues of CPVH41-18 (the acceptor antibody). Lastly, the framework IV sequences of CPVH41-18 replaced the corresponding framework IV residues of the 3G9 heavy chain variable region. The completed engineered 3G9 heavy chain V region is shown in SEQ ID NO: 78. Twelve donor framework residues were retained in the engineered heavy chain variable region at positions 24, 27, 30, 38, 48, 66–69, 71, 73, and 94.

EXAMPLE 9

Expression and Characterization of Engineered Anti-Erythropoietin Receptor Monoclonal Antibodies The engineered 3G9 antibody was expressed in cells using methods well known to those skilled in the art. Briefly, genes encoding the complete engineered 3G9 VH and Vκ regions were assembled from long synthetic oligonucleotides and ligated into appropriate eukaryotic expression vectors containing IgG1,κ antibody constant regions. The expression vector contained a selectable marker for neomycin resistance and CMV promoter regulatory sequences. Subsequent transfection of COS host cells resulted in the expression of engineered 3G9 (CP3G9).

Culture supernatants from COS cells transiently transfected with chimpanzee framework engineered 3G9 were compared with another 3G9 variant for the ability to bind human EPOr. The entire extracellular domain of the EPOr was expressed as recombinant protein, purified, and adsorbed onto the wells of ELISA plates. Dilutions of different antibodies were then tested for the ability to specifically bind to the solid phase associated EPOr.

HZ3G9 is a humanized variant of 3G9 in which human frameworks were used in traditional CDR grafting experiments. The humanized 3G9 heavy chain amino acid sequence is shown in SEQ ID NO: 79. The humanized 3G9 light chain sequence is shown in SEQ ID NO: 80. Previous experiments showed that HZ3G9 retained the full binding affinity and avidity of the parental murine 3G9. Accordingly, since HZ3G9G1 is identical to the chimpanzee version in all respects except the V region cassette, it was used in the present comparative binding experiments as a surrogate for murine 3G9. Negative control antibodies were also tested, including HZD12 which is a humanized antibody specific for human integrin, and CPB9 which is a chimpanzee framework engineered antibody specific for human integrins described above. Different concentrations of the 3G9 variants and control antibodies were incubated for one hour. After washing, the bound antibodies were detected by incubation with anti-human H+L antibody-enzyme conjugate, a final wash, and addition of chromagen.

The binding curves obtained for CP3G9 and HZ3G9 were superimposable. This result indicates that the human and the chimpanzee framework engineered versions of 3G9 have identical overall binding avidity for the specific antigen human EPOr. Since the constant regions of HZ3G9 and CP3G9 are identical, the results also suggest the full binding affinity of the original rodent 3G9 is retained in the chimpanzee version of 3G9. Accordingly, the results show that CDR grafting of rodent CDRs onto chimpanzee acceptor frameworks as described in the present invention retained the full binding avidity of the parental rodent antibody.

A BIAcore analysis (Pharmacia) was performed to determine the binding affinity for human EPOr of murine 3G9 and CP3G9. The interaction of CP3G9 as well as murine 3G9 with EPOr was characterized using a BIAcore 1000 biosensor. Descriptions of the instrumentation and the sensor surfaces are described in Brigham-Burke et al., *Anal. Biochem.*, 205:125–131 (1992).

CP3G9 was captured onto a sensor surface of immobilized protein A. The kinetic binding constants were determined by passing solutions of monomeric EPOr over the surface and monitoring binding versus time. The equilibrium dissociation constant for the interaction was then derived from the ratio of the kinetic constants. The parent murine 3G9 was captured onto a surface of protein A captured rabbit anti-mouse Fc specific polyclonal antibody. The kinetics and dissociation constant for the interaction with EPOr was determined as described above. All measurements were made in 10 mM sodium phosphate, 150 mM NaCl pH 7.23 mM EDTA and 0.005% Tween 20. The flow rate was 60 uL/min. The temperature was 20° C.

|  | $k_{ass}$ (M$^{-1}$s$^{-1}$) | $k_{diss}$ (s$^{-1}$) | $K_D$ (nM) |
| --- | --- | --- | --- |
| murine 3G9 | $1.2 \times 10^6$ | $4.0 \times 10^{-3}$ | 3.3 |
| CP3G9 | $1.0 \times 10^6$ | $9.1 \times 10^{-3}$ | 9.1 |

These results show that the dissociation equilibrium constants determined for the murine and chimpanzee framework versions of 3G9 are within three fold of each other. This data is in good agreement with the results of the ELISA-based study described above. Accordingly, the results show that the process used in generating the chimpanzee version of 3G9 largely retained the binding affinity of the original rodent mAb.

The present invention may be embodied in other specific forms without departing from the spirit or essential attributes thereof, and, accordingly, reference should be made to the appended claims, rather than to the foregoing specification, as indicating the scope of the invention.

What is claimed is:

1. An antibody comprising:
   a) a variable region comprising six complementarity determining regions (CDRs) from an antigen-specific donor antibody of a rodent and acceptor framework comprising amino acid residues from an Old World Ape, wherein at least one CDR-contacting amino acid residue from the acceptor framework is replaced with a corresponding residue from the donor framework, and wherein said CDR-contacting residue contacts a CDR residue within said antibody by the group selected from coming within the van der Waals radius of said CDR residue, a salt bridge and a hydrophobic interaction; and
   b) at least one constant region from human, and
   wherein said antibody has a specific binding avidity that is within about three-fold of the specific binding avidity of said antigen-specific donor antibody.

2. The antibody of claim 1, wherein the rodent is mouse.

3. The antibody of claim 1, wherein the rodent is rat.

4. The antibody of claim 1, wherein the Old World Ape is *Pan troglodytes, Pan paniscus* or *Gorilla gorilla*.

5. The antibody of claim 1, wherein the Old World Ape is *Pan troglodytes*.

6. The antibody of claim 1, wherein the acceptor framework comprises a light (VL) and heavy (VH) chain region each comprising four acceptor framework regions (framework I, II, III, and IV), and wherein the VH acceptor framework I, II, III and IV are from chimpanzee.

7. The antibody of claim 6, wherein the VH acceptor framework I, II and III comprise an amino acid sequence as set forth in SEQ ID NOs: 10, 11, 12, 13, 14, 15, 16, 17 or 18.

8. The antibody of claim 6, wherein the VH acceptor framework IV comprises an amino acid sequence as set forth in SEQ ID NOs: 81, 82, 83, 84 or 85.

9. The antibody of claim 1, wherein VL comprises segments Vκ and Vλ, and wherein Vκ comprises four acceptor framework regions (framework I, II, III, and IV), and wherein Vκ acceptor framework I, II, III and IV are from chimpanzee.

10. The antibody of claim 9, wherein Vκ acceptor framework I, II, and III comprise an amino acid sequence as set forth in SEQ ID NOs: 28, 29, 30, 31, 32, 33, 34, 35 or 36.

11. The antibody of claim 9, wherein Vκ acceptor framework IV comprises an amino acid sequence as set forth in SEQ ID NOs: 86 or 87.

12. The antibody of claim 1, wherein the amino acid sequence of the complete light chain is set forth in SEQ ID NO: 68 and the amino acid sequences of the heavy chain is set forth in SEQ ID NO: 70.

13. The antibody of claim 1, wherein the amino acid sequence of the complete light chain is set forth in SEQ ID NO: 73 and the amino acid sequences of the heavy chain is set forth in SEQ ID NO: 74.

14. The antibody of claim 1, wherein the amino acid sequence of the complete light chain is set forth in SEQ ID NO: 77 and the amino acid sequences of the heavy chain is set forth in SEQ ID NO: 78.

* * * * *